US007847060B2

(12) United States Patent
Tahara et al.

(10) Patent No.: US 7,847,060 B2
(45) Date of Patent: Dec. 7, 2010

(54) PEPTIDE VACCINES FOR LUNG CANCERS EXPRESSING TTK, URLC10 OR KOC1 POLYPEPTIDES

(75) Inventors: Hideaki Tahara, Tokyo (JP); Takuya Tsunoda, Tokyo (JP); Yusuke Nakamura, Tokyo (JP); Yataro Daigo, Tokyo (JP); Shuichi Nakatsuru, Kanagawa (JP)

(73) Assignee: Oncotherapy Science, Inc., Kanagawa (JP)

( * ) Notice: Subject to any disclaimer, the term of this patent is extended or adjusted under 35 U.S.C. 154(b) by 0 days.

(21) Appl. No.: 11/816,616

(22) PCT Filed: Feb. 17, 2006

(86) PCT No.: PCT/JP2006/303354

§ 371 (c)(1),
(2), (4) Date: Apr. 23, 2009

(87) PCT Pub. No.: WO2006/090810

PCT Pub. Date: Aug. 31, 2006

(65) Prior Publication Data

US 2009/0202576 A1 Aug. 13, 2009

Related U.S. Application Data

(60) Provisional application No. 60/656,857, filed on Feb. 25, 2005.

(51) Int. Cl.
*A61K 38/00* (2006.01)
*A61K 38/04* (2006.01)
*A61K 38/08* (2006.01)

(52) U.S. Cl. .................................. 530/300; 530/328
(58) Field of Classification Search ....................... None
See application file for complete search history.

(56) References Cited

U.S. PATENT DOCUMENTS

| 2002/0086848 | A1 | 7/2002 | Kubbies et al. | |
| 2003/0022858 | A1 | 1/2003 | Kubbies et al. | |
| 2003/0045491 | A1 | 3/2003 | Reinhard et al. | |
| 2003/0105000 | A1* | 6/2003 | Pero et al. | 514/12 |
| 2003/0232350 | A1* | 12/2003 | Afar et al. | 435/6 |
| 2003/0236209 | A1* | 12/2003 | Foy et al. | 514/44 |
| 2004/0005563 | A1* | 1/2004 | Mack et al. | 435/6 |
| 2005/0186610 | A1 | 8/2005 | Lee et al. | |
| 2006/0024692 | A1 | 2/2006 | Nakamura et al. | |

FOREIGN PATENT DOCUMENTS

| EP | 1854473 A1 | 1/2007 |
| JP | 2000-510002 A | 8/2000 |
| JP | 2005-523688 A | 8/2005 |
| JP | 2005-230011 A | 9/2005 |
| JP | 2005-525789 A | 9/2005 |
| JP | 2005-531280 A | 10/2005 |
| JP | 2006-500949 A | 1/2006 |
| JP | 2007-506443 A | 3/2007 |
| WO | WO 98/45428 A1 | 10/1998 |
| WO | WO 99/46594 A2 | 9/1999 |
| WO | WO 01/72775 A2 | 10/2001 |
| WO | WO 02/30268 A2 | 4/2002 |
| WO | WO 02/068444 A1 | 9/2002 |
| WO | WO 02/086443 A2 | 10/2002 |
| WO | WO 03/038130 A2 | 5/2003 |
| WO | WO 03/042661 A2 | 5/2003 |
| WO | WO 03/062395 A2 | 7/2003 |
| WO | WO 03/086175 A2 | 10/2003 |
| WO | WO 2004/031413 A2 | 4/2004 |
| WO | WO 2005/002509 A2 | 1/2005 |
| WO | WO 2005/073374 A1 | 8/2005 |
| WO | WO 2006/093337 A1 | 9/2006 |

OTHER PUBLICATIONS

Celis (J of Clinical Investigation, 2002, 110:1765-1768).*
Marincola et al. (Trends in Immunology, Jun. 2003, 334-341).*
Kirkin et al. (1998, APMIS, 106: 665-679).*
Sherman et al. (Critical Reviews in Immunol. 1998, 18:47-54).*
George et al. (2005, Trends in Immunology 26(12):653-659).*
Smith (Clin. Immunol, 1994, 41(4): 841-849).*
Harlin et al. (Caner Immunol. Immunotherap. 2006, 55:1185-1197).*
Gura (Science, 1997, 278:1041-1042).*
Kaiser (Science 2006, 31: 1370).*
Bowie et al (Science, 1990, 247:1306-1310).*
Skolnick et al. (TIBTECH 18:34-39, 2000).*
Ibragimova and Eade (Biophysical Journal, Oct. 1999, vol. 77, pp. 2191-2198).*
Rudikoff et al. (PNAS, USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444).*
Adams, H-P., "Prediction of binding to MHC class I molecules," *Journal of Immunological Methods*, vol. 185(2), pp. 181-190 (Sep. 25, 1995).
Schueler-Furman, O., et al., "Structure-based prediction of binding peptides to MHC class I molecules: Application to a broad range of MHC alleles," *Protein Science*, vol. 9(9), pp. 1838-1846 (Sep. 2000).
Tokunaga, K., et al., "Sequence-based association analysis of HLA class I and II alleles in Japanese supports conservation of common haplotypes," *Immunogenetics*, vol. 46(3), pp. 199-205 (1997).

(Continued)

*Primary Examiner*—Peter J Reddig
(74) *Attorney, Agent, or Firm*—Townsend and Townsend and Crew LLP

(57) ABSTRACT

The present invention provides peptides comprising the amino acid sequence of SEQ ID NO: 8, 67, 89, as well as peptides comprising the above-mentioned amino acid sequences in which 1, 2, or several amino acids are substituted, deleted, or added, and having cytotoxic T cell inducibility. The present invention also provides drugs for treating or preventing tumors comprising these peptides. The peptides of the present invention can also be used as vaccines.

2 Claims, 12 Drawing Sheets

OTHER PUBLICATIONS

Kondo et al.; "Prominent roles of secondary anchor residues in peptide binding to HLA-A24 human class 1 molecules"; 1995; *J. Immunol.*; vol. 155, No. 9, pp. 4307-4312.

Kubo et al.; "Definition of specific peptide motifs for four major HLA-A alleles"; 1994; *J. Immunol.*; vol. 152, No. 8, pp. 3913-3924.

Zaremba et al.; "Identification of an enhancer agonist cytotoxic T lymphocyte peptide from human carcinoembryonic antigen"; 1997; *Cancer Res.*; vol. 57, pp. 4750-4757.

Mills, G., et al., "Expression of TTK, a novel human protein kinase, is associated with cell proliferation," *The Journal of Biological Chemistry*, vol. 267(22), pp. 16000-16006 (1992).

Wang, T., et al., "Identification of genes using differentially overexpressed in lung squamous cell carcinoma using combination of cDNA subtraction and microarray analysis," *Oncogene*, vol. 19, pp. 1519-1528 (2000).

Schmandt et al., "IL-2 induced expression of TTK, a serine, threonine, tyrosine kinase, correlates with cell cycle progression"; *J. Immunol.*; 152: 96-105 (1994).

Stucke et al.; "Human Mps1 kinase is required for the spindle assembly checkpoint not for centrosome duplication"; *EMBO J.*; 21(7): 1723-1732 (2002).

Wiess et al.; "The *Saccharomyces cerevisiae* spindle pole body duplication gene MPS1 is a part of the mitotic checkpoint"; *J. Cell. Biol.*; 132(1-2): 111-123 (1996).

Winey et al.; "*MPS1* and *MPS2*: Novel yeast genes defining distinct steps of spindle pole body duplication"; *J. Cell. Biol.*; 114(4): 745-754 (1991).

Rammensee, H-G, et al., "MHC ligands and peptide motifs: first listing," *Immunogenetics*, vol. 41(4), pp. 178-228 (1995).

\* cited by examiner

US 7,847,060 B2

PEPTIDE VACCINES FOR LUNG CANCERS EXPRESSING TTK, URLC10 OR KOC1 POLYPEPTIDES

CROSS-REFERENCES TO RELATED APPLICATIONS

This application is a U.S. National Stage Application of PCT/JP2006/303354, filed Feb. 17, 2006, which claims the benefit of U.S. Provisional Application Ser. No. 60/656,857 filed Feb. 25, 2005, all of which are hereby incorporated by reference in their entirety.

TECHNICAL FIELD

The present invention relates to the field of biological science, more specifically to the field of cancer therapy. In particular, the present invention relates to novel peptides that are extremely effective as cancer vaccines, and drugs for treating and preventing tumors that contain these peptides.

BACKGROUND ART

Lung cancer is one of the most commonly fatal human tumors. Many genetic alterations associated with the development and progression of lung cancer have been reported. Genetic changes can aid prognostic efforts and predictions of metastatic risk or response to certain treatments. (Mitsudomi T et al., (2000) Clin Cancer Res 6: 4055-63; Niklinski et al., (2001) Lung Cancer. 34 Suppl 2: S53-8; Watine J. (2000) Bmj 320: 379-80). Non-small cell lung cancer (NSCLC) is by far the most common form of lung cancer, accounting for nearly 80% of lung tumors (Society, A. C. Cancer Facts and FIGS. 2001, 2001). The overall 10-year survival rate remains as low as 10%, despite recent advances in multi-modality therapy, because the majority of NSCLCs are not diagnosed until advanced stages (Fry, W. A. et al., (1999) Cancer. 86: 1867-76). Although chemotherapy regimens based on platinum are considered the reference standards for treatment of NSCLC, those drugs are able to extend survival of patients with advanced NSCLC only about six weeks (Non-small Cell Lung Cancer Collaborative Group, (1995) BMJ. 311: 899-909). Numerous targeted therapies are being investigated for this disease, including tyrosine kinase inhibitors; however, to date promising results have been achieved in only a limited number of patients and some recipients suffer severe adverse reactions (Kris M G, et al., (2002) Proc Am Soc Clin Oncol. 21: 292a(A1166)).

It has been demonstrated that CD8+ cytotoxic T lymphocytes (CTLs) recognize epitope peptides derived from tumor-associated antigens (TAAs) presented on MHC class I molecules, and lyse the tumor cells. Since the discovery of the MAGE family as the first example of TAAs, many other TAAs have been discovered using immunological approaches (Boon T. (1993) Int J Cancer 54: 177-80; Boon T. et al., (1996) J Exp Med 183: 725-9; van der Bruggen P et al., (1991) Science 254: 1643-47; Brichard V et al., (1993) J Exp Med 178: 489-95; Kawakami Y et al., (1994) J Exp Med 180: 347-52). Some of them are now in clinical development as targets of immunotherapy. TAAs discovered so far include MAGE (van der Bruggen P et al., (1991) Science 254: 1643-7), gp100 (Kawakami Y et al., (1994) J Exp Med 180: 347-52), SART (Shichijo S et al., (1998) J Exp Med 187:277-88), and NY-ESO-1 (Chen Y. T. et al., (1997) Proc. Natl. Acd. Sci. USA, 94: 1914-8). On the other hand, certain gene products demonstrated to be somewhat specifically over-expressed in tumor cells have been shown to be recognized as targets inducing cellular immune responses. Such gene products include p53 (Umano Y et al., (2001) Br J Cancer, 84:1052-7), HER2/neu (Tanaka H et al., (2001) Br J Cancer, 84: 94-9), CEA (Nukaya I et al., (1999) Int. J. Cancer 80, 92-7) and the like.

Despite significant progress in basic and clinical research concerning TAAs (Rosenberg S A et al., (1998) Nature Med, 4: 321-7; Mukherji B. et al., (1995) Proc Natl Acad Sci USA, 92: 8078-82: Hu X et al., (1996) Cancer Res, 56: 2479-83), only a very limited number of candidate TAAs suitable for treatment of adenocarcinomas, such as lung cancer, are available. TAAs that are abundantly expressed in cancer cells, and whose expression is restricted to cancer cells, would be promising candidates as immunotherapeutic targets.

It has been repeatedly shown in $^{51}$Cr-release assays that peptide-stimulated peripheral blood mononuclear cells (PBMCs) from certain healthy donors produce significant levels of IFN-γ in response to the peptide, but rarely exert cytotoxicity against tumor cells in an HLA-A24 or A0201 restricted manner (Kawano K et al., (2000) Cancer Res 60: 3550-8; Nishizaka et al., (2000) Cancer Res 60: 4830-7; Tamura et al., (2001) Jpn J Cancer Res 92: 762-7). However, both HLA-A24 and HLA-A0201 are common HLA alleles in Japanese and Caucasian populations (Date Y et al., (1996) Tissue Antigens 47:93-101; Kondo A et al., (1995) J Immunol 155:4307-12; Kubo R T et al., (1994) J Immunol 152: 3913-24; Imanishi et al., Proceeding of the eleventh International Histocompatibility Workshop and Conference Oxford University Press, Oxford, 1065 (1992); Williams F et al., (1997) Tissue Antigen 49:129). Thus, antigenic peptides of cancers presented by these HLA alleles may be especially useful for the treatment of cancers among Japanese and Caucasian patients. Further, it is known that the induction of low-affinity CTL in vitro usually results from the use of peptide at a high concentration, generating a high level of specific peptide/MHC complexes on antigen-presenting cells (APCs), which will effectively activate these CTL (Alexander-Miller et al., (1996) Proc Natl Acad Sci USA 93: 4102-7).

Recent developments in cDNA microarray technologies have enabled the constructions of comprehensive profiles of gene expression of malignant cells as compared to normal cells (Okabe, H. et al., (2001) Cancer Res., 61, 2129-37; Lin Y M. et al., (2002) Oncogene, 21; 4120-8; Hasegawa S. et al., (2002) Cancer Res 62:7012-7). This approach enables an understanding of the complex nature of cancer cells and the mechanisms of carcinogenesis and facilitates the identification of genes whose expression is deregulated in tumors (Bienz M. et al., (2000) Cell 103, 311-320). Among the transcripts identified as commonly up-regulated in lung cancers, TTK (TTK Protein kinase; GenBank Accession No. NM_003318; SEQ ID Nos. 1, 2), URLC10 (cDNA for differentially expressed CO16 gene; GenBank Accession No. AB105187; SEQ ID Nos.3, 4) and KOC1 (IGF II mRNA Binding Protein 3; GenBank Accession No. NM_006547; SEQ ID Nos.5, 6) are of particular interest to the present inventors, being specifically up-regulated in tumor cells of the lung cancer tissues in more than 80% of the cases analyzed. In contrast, Northern blot analysis demonstrated that these gene products are not found in normal vital organs (See WO2004/031413, the entire contents of which are incorporated by reference herein). Thus, immunogenic peptides derived from TTK, URLC10 and KOC1 may find utility in killing tumor cells expressing those antigens. The present invention addresses these and other needs.

SUMMARY OF THE INVENTION

Three genes, TTK (TTK Protein kinase), URLC10 (cDNA for differentially expressed CO16 gene) and KOC1 (IGF II mRNA Binding Protein 3) have been identified as up-regulated in lung cancer. The genes were identified using gene expression profiling with a genome-wide cDNA microarray containing 23,040 genes. As discussed above, expression of TTK, URLC10 and KOC1 is specifically up-regulated in tumor cells in more than 80% of the patients with lung cancer yet absent in other normal vital organs.

The present invention is based, at least in part, on the identification of epitope peptides of the gene products of these genes (TTK, URLC10, and KOC1) which elicit cytotoxic T lymphocytes (CTLs) specific to the corresponding molecules. As discussed in detail below, Peripheral Blood Mononuclear Cells (PBMC) of healthy donor were stimulated using HLA-A*2402 binding candidate peptides derived from TTK, URLC10 or KOC1. CTL clones were then established with specific cytotoxicity against the HLA-A24 positive target cells pulsed with each of the candidate peptides. Further analysis of the CTL clones showed the potent cytotoxic activity against, not only the peptide-pulsed target cells, but also tumor cells that endogenously express TTK, URLC10 or KOC1. Furthermore, both a cold target inhibition assay and an antibody blocking assay revealed that CTL cell clones specifically recognized the MHC class I-peptide complex. These results demonstrate that these peptides are HLA-A24 restricted epitope peptides that can induce potent and specific immune responses against lung cancer cells expressing TTK, URLC10 or KOC1.

Accordingly, the present invention provides methods for treating or preventing lung cancer in a subject comprising the step of administering to the subject the TTK, URLC10 and KOC1 polypeptides of the invention. Anti-tumor immunity is induced by the administration of these polypeptides. Thus, the present invention provides methods for inducing anti-tumor immunity in a subject comprising the step of administering to the subject the TTK, URLC10 and KOC1 polypeptides, as well as pharmaceutical compositions for treating or preventing lung cancer comprising the TTK, URLC10 and KOC1 polypeptides.

These and other objects and features of the invention will become more fully apparent when the following detailed description is read in conjunction with the accompanying figures and examples. However, it is to be understood that both the foregoing summary of the invention and the following detailed description are of preferred embodiments, and not restrictive of the invention or other alternate embodiments of the invention.

DETAILED DESCRIPTION OF THE INVENTION

Figure 1:
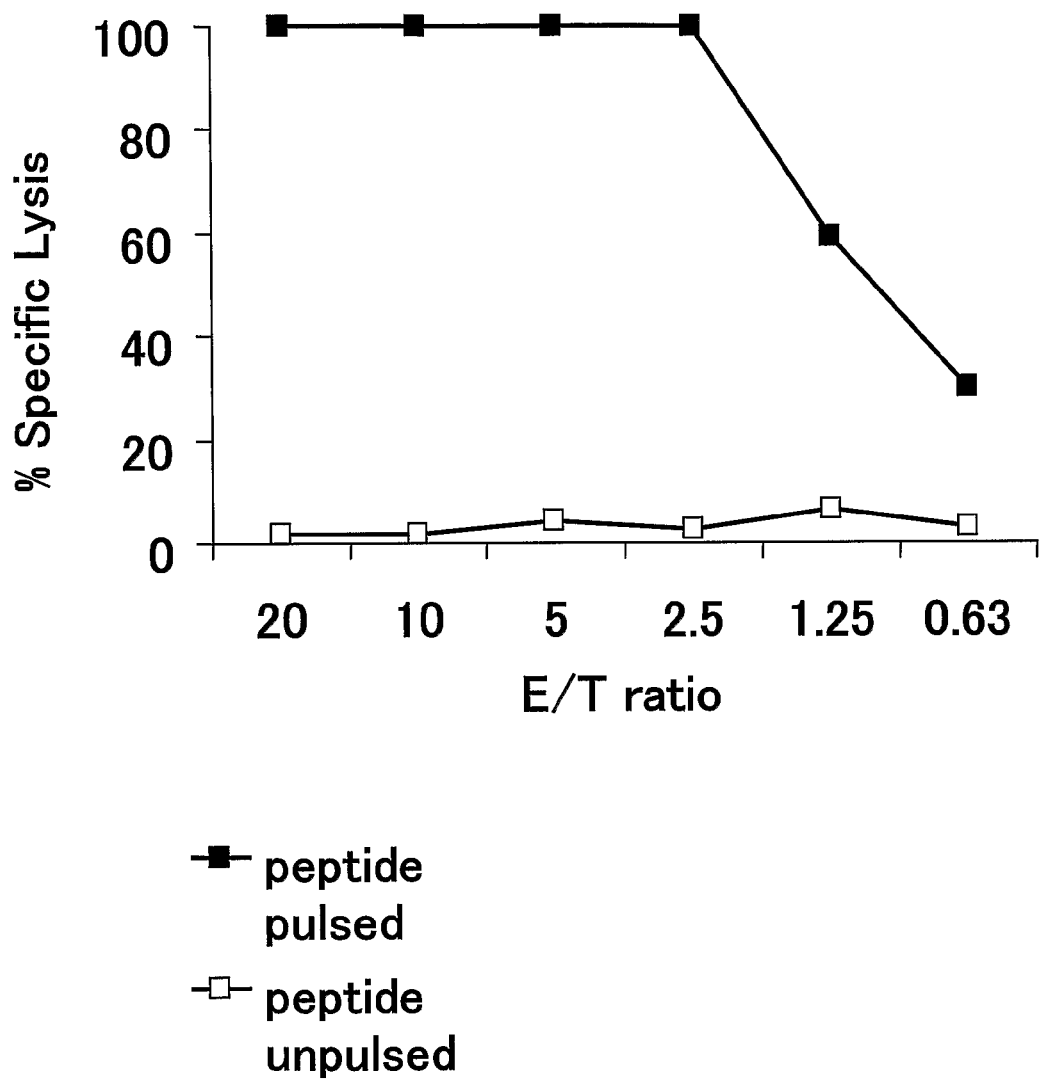
FIG. 1 is a graph showing that the CTL clone raised by TTK-567 has peptide-specific cytotoxicity. Specifically, the CTL clone showed high cytotoxic activity against target cells (A24LCL) pulsed with TTK-567, whereas it did not show significant cytotoxic activity against the same target cells (A24LCL) pulsed with no peptides.

The words "a", "an", and "the" as used herein mean "at least one" unless otherwise specifically indicated.

Unless otherwise defined, all technical and scientific terms used herein have the same meaning as commonly understood by one of ordinary skill in the art to which this invention belongs.

Identification of new TAAs, particularly those that induce potent and specific anti-tumor immune responses, warrants further development of the clinical application of the peptide vaccination strategy in various types of cancer (Boon T et al., (1996) J Exp Med 183: 725-9; van der Bruggen P et al., (1991) Science 254: 1643-7; Brichard V et al., (1993) J Exp Med 178: 489-95; Kawakami Y et al., (1994) J Exp Med 180: 347-52; Shichijo S et al., (1998) J Exp Med 187:277-88; Chen Y T et al., (1997) *Proc. Natl. Acd. Sci.* USA, 94: 1914-8; Harris C C, (1996) *J Natl Cancer Inst* 88:1442-5; Butterfield L H et al., (1999) *Cancer Res* 59:3134-42; Vissers J L et al., (1999) *Cancer Res* 59: 5554-9; van der Burg S H et al., (1996) *J. Immunol* 156:3308-14; Tanaka F et al., (1997) *Cancer Res* 57:4465-8; Fujie T et al., (1999) *Int J Cancer* 80:169-72; Kikuchi M et al., (1999) *Int J Cancer* 81: 459-66; Oiso M et al., (1999) *Int J Cancer* 81:387-94). As noted above, TTK, URLC10 and KOC1 were previously identified as over-expressed in lung cancer using cDNA microarray technologies. As discussed in WO2004/031413, TTK encodes an S_TKc domain. The protein encoded by the TTK gene phosphorylates proteins on serine, threonine and tyrosine, such phosphorylation likely associated with cell proliferation (Mills G B et al., (1992) J Biol Chem 267: 16000-6; Schmandt R et al., (1994) J Immunol.; 152(1):96-105; Stucke V M et al., (2002) EMBO J.; 21(7):1723-32). KOC1 encodes insulin-like growth factor 2 (IGF2) mRNA-binding protein 3 (IMP-3). IMP-3 protein contains 2 functional RNA recognition motifs (RRM) in addition to the 4 KH domains. The protein associates specifically with the 5-prime UTR of the human 6.0-kb insulin-like growth factor II (IGF2) leader-3 mRNA, suggesting a role for IMP-3 in the physiologic regulation of IGF2 production. (Nielsen, J. et al., (1999) *Molec. Cell. Biol.* 19: 1262-1270) IMP-3 was also over-expressed in pancreatic cancers (Mueller-Pillasch, F. et al., (1997) *Oncogene* 14: 2729-2733).

Previous experiments demonstrated that TTK, URLC10 and KOC1 were over-expressed in lung cancer and show minimal expression in normal tissues. In addition, these genes were shown to have a significant function related to cell proliferation (See WO2004/031413).

In the present invention, peptides derived from TTK, URLC10 or KOC1 are shown to be TAA epitopes restricted by HLA-A24, an HLA allele commonly found in the Japanese and Caucasian populations. Specifically, using their binding affinities to HLA-A24, candidates of HLA-A24 binding peptides derived from TTK, URLC10 or KOC1 were identified. After the in vitro stimulation of T-cells by dendritic cells (DCs) loaded with these peptides, CTLs were successfully established using TTK-567 (SYRNEIAYL (SEQ ID No.8)), URLC10-177 (RYCNLEGPPI (SEQ ID No.67)) and KOC1-508 (KTVNELQNL (SEQ ID No.89)). These CTLs showed potent cytotoxic activity against the peptide-pulsed A24LCL cells. Furthermore, CTL clones derived from these cells also showed specific cytotoxicity against HLA-A24 positive lung carcinoma cell lines that endogenously over-express TTK, URLC10 or KOC1. However, these CTL clones did not show cytotoxic activity against cell lines lacking expression of either HLA-A24 or target TAA. The specific cytotoxic activities of these CTL clones were significantly inhibited by the cold target. These results demonstrate that TTK, URLC10 and KOC1 are useful as TAAs of lung cancer cells and that TTK-567, KOC1-508 and URLC10-177 are epitope peptides of each TAA restricted by HLA-A24. Since these antigens are over-expressed in most lung cancers and are associated with tumor cell proliferation, they find utility as immunotherapeutic targets against lung cancers.

Accordingly, the present invention further provides methods of treating or preventing lung cancer in a subject, said methods comprising the steps of administering an immunogenic peptide of less than about 40 amino acids, often less than about 20 amino acids, usually less than about 15 amino acids and comprising the amino acid sequence of SEQ ID NOs: 8, 67, or 89 to the subject in need thereof. Alternatively, the immunogenic peptide may comprise a sequence of SEQ ID NOs: 8, 67, or 89 in which 1, 2, or several amino acids are substituted, deleted or added, provided the resulting variant peptide retains the immunogenic activity (i.e., the ability to induce CTLs specific to lung cancer cells). The number of residues to be substituted, deleted, or added is generally 5 amino acids or less, preferably 4 amino acids or less, more preferably 3 amino acids or less, even more preferably one or two amino acids.

Variant peptides (i.e., peptides comprising an amino acid sequence modified by substituting, deleting, or adding one, two or several amino acid residues to an original amino acid sequence) have been known to retain the original biological activity (Mark D F et al., (1984) Proc Natl Acad Sci USA 81: 5662-6; Zoller M J and Smith M, (1982) Nucleic Acids Res 10:6487-500; Dalbadie-McFarland G et al., (1982) Proc Natl Acad Sci USA 79: 6409-13). In the context of the present invention, the amino acid modification results in conservation of the properties of the original amino acid side-chain (a process known as conservative amino acid substitution). Examples of properties of amino acid side chains are hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). Note, the parenthetic letters indicate the one-letter codes of amino acids.

In preferred embodiments, the immunogenic peptide is a nonapeptide (9-mer) or a decapeptide (10-mer).

The present invention further provides a method of inducing anti-tumor immunity for lung cancer in a subject, said method comprising the steps of administering to the subject an immunogenic peptide of the invention, namely one comprising the amino acid sequence of SEQ ID NOs: 8, 67, or 89 or a variant thereof (i.e., including 1, 2, or several amino acid substitutions, deletions, or additions) to the subject in need thereof.

In the context of the present invention, the subject is preferably a mammal. Exemplary mammals include, but are not limited to, e.g., a human, non-human primate, mouse, rat, dog, cat, horse, or cow.

In the present invention, the peptide can be administered to a subject via in vivo or ex vivo. Furthermore, the present invention also provides use of nonapeptide or decapeptide selected from peptides comprising the amino acid sequence of SEQ ID NOs: 8, 67, and 89 (and variants thereof) for manufacturing an immunogenic composition for treating or preventing lung cancer.

Homology analyses of TTK-567, KOC1-508 and URLC10-177 demonstrate that they do not have significant homology with the peptides derived from any known human gene products. Accordingly, the possibility of unknown or undesirable immune responses with immunotherapy against these molecules is significantly reduced.

Regarding HLA antigens, the use of an A-24 type that is highly expressed among the Japanese population is favorable for obtaining effective results, and the use of subtypes, such as A-2402, is even more preferable. Typically, in the clinic, the type of HLA antigen of the patient requiring treatment is investigated in advance, which enables the appropriate selection of peptides having high levels of binding affinity to this antigen, or having cytotoxic T cell (CTL) inducibility by antigen presentation. Furthermore, in order to obtain peptides showing high binding affinity and CTL inducibility, substitution, deletion, or addition of 1, 2, or several amino acids may be performed based on the amino acid sequence of the naturally occurring TTK, URLC10 and KOC1 partial peptide. Herein, the term "several" means refers to 5 or less, more preferably 3 or less. Furthermore, in addition to peptides that are naturally displayed, since the regularity of the sequences of peptides displayed by binding to HLA antigens is already known (Kubo R T, et al., (1994) J. Immunol., 152, 3913-24; Rammensee H G; et al., (1995) Immunogenetics. 41:178-228; Kondo A, et al., (1995) J. Immunol. 155:4307-12), modifications based on such regularity can be performed on the immunogenic peptides of the invention. For example, peptides showing high HLA-24 binding affinity in which the second amino acid from the N terminus substituted with phenylalanine, tyrosine, methionine, or tryptophan may be favorably used. Likewise, peptides whose C-terminal amino acid is substituted with phenylalanine, leucine, isoleucine, tryptophan, or methionine may also be used favorably.

However, when the peptide sequence is identical to a portion of the amino acid sequence of an endogenous or exogenous protein having a different function, side effects such as autoimmune disorders or allergic symptoms against specific substances may be induced. Therefore, it is preferable to avoid the situation wherein the immunogenic sequence matches the amino acid sequence of a known protein. This situation may be avoided by performing a homology search using available databases. If homology searches confirm that peptides in which 1, 2 or several different amino acids do not exist, then the danger that modifications of the above-mentioned amino acid sequence that, for example, increase the binding affinity with HLA antigens, and/or increase the CTL inducibility can be avoided.

Although peptides having high binding affinity to the HLA antigens as described above are expected to be highly effective as cancer vaccines, the candidate peptides, which are selected according to the presence of high binding affinity as an indicator, must be examined for the actual presence of CTL inducibility. CTL inducibility may be confirmed by inducing antigen-presenting cells carrying human MHC antigens (for example, B-lymphocytes, macrophages, and dendritic cells), or more specifically dendritic cells derived from human peripheral blood mononuclear leukocytes, and, after stimulation with the peptide of interest, mixing with CD8-positive cells and measuring the cytotoxic activity against the target cells. As the reaction system, transgenic animals produced to express a human HLA antigen (for example, those described in BenMohamed L, et al., (2000) Hum. Immunol.; 61(8):764-79 Related Articles, Books, Linkout.) may be used. For example, the target cells can be radio-labeled with $^{51}$Cr and such, and cytotoxic activity can be calculated from radioactivity released from the target cells. Alternatively, it can be examined by measuring IFN-γ produced and released by CTL in the presence of antigen-presenting cells that carry immobilized peptides, and visualizing the inhibition zone on the media using anti-IFN-γ monoclonal antibodies.

As a result of examining the CTL inducibility of peptides as described above, it was discovered that peptides having high binding affinity to an HLA antigen did not necessarily have high inducibility. However, nonapeptides or decapeptides selected from peptides comprising the amino acid sequences indicated by SYRNEIAYL (SEQ ID NO: 8), RYCNLEGPPI (SEQ ID NO: 67), KTVNELQNL (SEQ ID NO: 89) showed particularly high CTL inducibility.

As noted above, the present invention provides peptides having cytotoxic T cell inducibility, namely those comprising the amino acid sequence of SEQ ID NOS: 8, 67, or 89 or a variant thereof (i.e., those in which 1, 2, or several amino acids are substituted, deleted, or added). It is preferably that the amino acid sequence comprise 9 or 10 amino acids indicated in SEQ ID NOS: 8, 67, 89 or a variant thereof do not match an amino acid sequence associated with another endogenous protein. In particular, amino acid substitution to phenylalanine, tyrosine, methionine, or tryptophan at the second amino acid from the N terminus, and to phenylalanine, leucine, isoleucine, tryptophan, or methionine at the C-terminal amino acid, and amino acid addition of 1 to 2 amino acids at the N terminus and/or C terminus are favorable examples.

Peptides of the present invention can be prepared using well known techniques. For example, the peptides can be prepared synthetically, using either recombinant DNA technology or chemical synthesis. Peptides of the present invention may be synthesized individually or as longer polypeptides comprising two or more peptides. The peptides of the present invention are preferably isolated, i.e., substantially free of other naturally occurring host cell proteins and fragments thereof.

The peptides of the present invention may contain modifications, such as glycosylation, side chain oxidation, or phosphorylation; so long as the modifications do not destroy the biological activity of the peptides as described herein. Other modifications include incorporation of D-amino acids or other amino acid mimetics that can be used, for example, to increase the serum half life of the peptides.

The peptides of this invention can be prepared as a combination, which comprises two or more of peptides of the invention, for use as a cancer vaccine that may induce CTL in vivo. The peptides may be in a cocktail or may be conjugated to each other using standard techniques. For example, the peptides can be expressed as a single polypeptide sequence. The peptides in the combination may be the same or different. By administering the peptides of this invention, the peptides are presented at a high density on the HLA antigens of antigen-presenting cells, which, in turn, induces CTLs that specifically react toward the complex formed between the displayed peptide and the HLA antigen. Alternatively, antigen-presenting cells having immobilized the peptides of this invention on their cell surface, obtained by removing dendritic cells from the subjects, may be stimulated by the peptides of this invention. Re-administration of these cells to the respective subjects induces CTL, and, as a result, aggressiveness towards the target cells can be increased.

More specifically, the present invention provides drugs for treating tumors or preventing proliferation, metastasis, and such of tumors, which comprise one or more of peptides of this invention. The peptides of this invention find particular utility in the treatment of tumors, such as lung cancer.

The peptides of this invention can be administered to a subject directly, as a pharmaceutical composition that has been formulated by conventional formulation methods. In such cases, in addition to the peptides of this invention, carriers, excipients, and such that are ordinarily used for drugs can be included as appropriate, without particular limitations. The immunogenic compositions of this invention may be used for treatment and prevention of various tumors, including lung cancers.

The immunogenic compositions for treatment and/or prevention of tumors, which comprise as the active ingredient one or more peptides of the present invention, can further include an adjuvant so that cellular immunity will be established effectively. Alternatively, they may be administered with other active ingredients, such as anti-tumor agents. Suitable formulations include granules. Suitable adjuvants are described in the literature (Johnson A G. (1994) Clin. Microbiol. Rev., 7:277-89). Exemplary adjuvants include, but are not limited to, aluminum phosphate, aluminum hydroxide, and alum. Furthermore, liposome formulations, granular formulations in which the drug is bound to few-μm diameter beads, and formulations in which a lipid is bound to the peptide may be conveniently used. The method of administration may be oral, intradermal, subcutaneous, intravenous injection, or such, and may include systemic administration or local administration to the vicinity of the targeted tumor. The dose of the peptide(s) of this invention can be adjusted appropriately according to the disease to be treated, age of the patient, weight, method of administration, and such. Though the dosage is ordinarily 0.001 mg to 1000 mg, preferably 0.01 mg to 100 mg, more preferably 0.1 mg to 10 mg, preferably administered once in a few days to few months, one skilled in the art can readily select the appropriate dose and method of administration, as, the selection and optimization of these parameters is well within routine skill.

The present invention further provides intracellular vesicles called exosomes, which present complexes formed between the peptides of this invention and HLA antigens on their surface. Exosomes can be prepared, for example, by using the methods described in detail in Published Japanese Translation of International Publication Nos. Hei 11-510507 and 2000-512161, and are preferably prepared using antigen-presenting cells obtained from subjects who are targets of treatment and/or prevention. The exosomes of this invention can be inoculated as cancer vaccines, similarly to the peptides of this invention.

The type of HLA antigens used must match that of the subject requiring treatment and/or prevention. For example, in the Japanese population, HLA-A24, particularly HLA-A2402, is often appropriate.

In some embodiments, the vaccine compositions of the present invention include a component which primes cytotoxic T lymphocytes. Lipids have been identified as agents capable of priming CTL in vivo against viral antigens. For example, palmitic acid residues can be attached to the ε- and α-amino groups of a lysine residue and then linked to an immunogenic peptide of the invention. The lipidated peptide can then be administered either directly, in a micelle or particle, incorporated into a liposome, or emulsified in an adjuvant. As another example of a lipid priming of CTL responses, E. coli lipoproteins, such as tripalmitoyl-S-glycerylcysteinlyseryl-serine (P3CSS), can be used to prime CTL when covalently attached to an appropriate peptide (see, e.g., Deres K, et al., (1989) Nature 342:561-4).

The immunogenic compositions of the present invention may also comprise nucleic acids encoding one or more of the immunogenic peptides disclosed here. See, e.g., Wolff J A et al., (1990) Science 247:1465-8; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

The immunogenic peptides of the invention can also be expressed by viral or bacterial vectors. Examples of suitable expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another suitable vector is BCG (Bacille Calmette Guerin). BCG vectors are described in Stover C K, et al., (1991) Nature 351:456-60. A wide variety of other vectors useful for therapeutic administration or immunization e.g., adeno and adeno-associated virus vectors, retroviral vectors, Salmonella typhi vectors, detoxified anthrax toxin vectors, and the like, are known in the art. See, e.g., Shata M T, et al., (2000) Mol. Med. Today 6:66-71; Shedlock D J and Weiner D B., et al., (2000) J. Leukoc. Biol. 68:793-806; and Hipp J D, et al., (2000) In Vivo 14:571-85.

The present invention also provides methods of inducing antigen-presenting cells using one or more peptides of this invention. The antigen-presenting cells can be induced by inducing dendritic cells from the peripheral blood monocytes and then contacting (stimulating) them with one or more peptides of this invention in vitro, ex vivo or in vivo. When peptides of the present invention are administered to the subjects, antigen-presenting cells that have the peptides of this invention immobilized to them are induced in the body of the subject. Alternatively, after immobilizing the peptides of this invention to the antigen-presenting cells, the cells can be administered to the subject as a vaccine. For example, the ex vivo administration may comprise steps of:

a: collecting antigen-presenting cells from a subject, and b: contacting the antigen-presenting cells of step a with a peptide of the present invention.

The antigen-presenting cells obtained by step b can be administered to the subject as a vaccine.

This invention also provides a method for inducing antigen-presenting cells having a high level of cytotoxic T cell inducibility, in which the method comprises the step of transferring genes comprising polynucleotide(s) encoding one or more peptides of this invention to antigen-presenting cells in vitro. The introduced genes may be in the form of DNAs or RNAs. For the method of introduction, without particular limitations, various methods conventionally performed in this field, such as lipofection, electroporation, and calcium phosphate method may be suitably used. More specifically, transfection may be performed as described in Reeves M E, et al., (1996) Cancer Res., 56:5672-7; Butterfield L H, et al., (1998) J. Immunol., 161:5607-13; Boczkowski D, et al., (1996) J. Exp. Med., 184:465-72; Published Japanese Translation of International Publication No. 2000-509281. By transferring the gene into antigen-presenting cells, the gene undergoes transcription, translation, and such in the cell, and then the obtained protein is processed by MHC Class I or Class II, and proceeds through a presentation pathway to present partial peptides.

The present invention further provides methods for inducing CTL using one or more peptides of this invention. When the peptides of this invention are administered to a subject, CTL are induced in the body of the subject, and the strength of the immune system targeting the lung cancer cells in the tumor tissues is thereby enhanced. Alternatively, the peptides of the present invention may be used in the context of an ex vivo therapeutic method, in which subject-derived antigen-presenting cells and CD8-positive cells or peripheral blood mononuclear leukocytes are contacted (stimulated) with one or more peptides of this invention in vitro, and, after inducing CTL, the cells are returned to the subject. For example, the method may comprise steps of:

a: collecting antigen-presenting cells from a subject, b: contacting the antigen-presenting cells of step a with a peptide of the present invention, c: mixing the antigen-presenting cells of step b with $CD^{8+}$ T cells and co-culturing so as to induce cytotoxic T-cells, and d: collecting $CD^{8+}$ T cells from the co-culture of step c.

The $CD^{8+}$ T cells having cytotoxic activity obtained by step d can be administered to the subject as a vaccine.

The present invention further provides isolated cytotoxic T cells induced using the peptides of this invention. The cytotoxic T cells, induced by stimulation with an antigen-presenting cell presenting one or more peptides of this invention, are preferably derived from subjects who are the target of treatment and/or prevention, and can be administered alone or in combination with other drugs, including one or more peptides of this invention or exosomes having anti-tumor activity. The obtained cytotoxic T cells act specifically against target cells presenting the peptides of this invention, or preferably the same peptide(s) used for induction. The target cells may be cells that express TTK, URLC10 and KOC1 endogenously, or cells that are transfected with TTK, URLC10 and KOC1 genes. Cells that present the peptides of this invention on the cell surface, due to stimulation with these peptides, can also become targets of attack.

The present invention also provides antigen-presenting cells presenting complexes formed between HLA antigens and one or more peptides of this invention. The antigen-presenting cells, obtained through contact with the peptides of this invention or the nucleotides encoding such peptides, are preferably derived from subjects who are the target of treatment and/or prevention, and can be administered as vaccines, alone or in combination with other drugs, including the peptides, exosomes, or cytotoxic T cells of the present invention.

In the context of the present invention, the term "vaccine" (also referred to as an immunogenic composition) refers to a substance that induces anti-tumor immunity or suppresses lung cancer upon inoculation into animals. According to the present invention, polypeptides comprising the amino acid sequence of SEQ ID NO: 8, 67, or 89 were suggested to be HLA-A24 restricted epitope peptides that may induce potent and specific immune response against lung cancer cells expressing TTK, URLC10 or KOC1. Thus, the present invention also encompasses a method of inducing anti-tumor immunity using polypeptides comprising the amino acid sequence of SEQ ID NO: 8, 67, or 89 or a variant thereof (i.e., including 1, 2, or several amino acid substitutions, deletions, or additions). In general, anti-tumor immunity includes immune responses such as follows:

induction of cytotoxic lymphocytes against tumors comprising cells expressing TTK, URLC10, or KOC1, induction of antibodies that recognize tumors comprising cells expressing TTK, URLC10, or KOC1, and induction of anti-tumor cytokine production.

Therefore, when a certain peptide induces any one of these immune responses upon inoculation into an animal, the peptide is decided to have anti-tumor immunity inducing effect. The induction of the anti-tumor immunity by a peptide can be detected by observing in vivo or in vitro the response of the immune system in the host against the peptide.

For example, a method for detecting the induction of cytotoxic T lymphocytes is well known. A foreign substance that enters the living body is presented to T cells and B cells by the action of antigen-presenting cells (APCs). T cells that respond to the antigen presented by APC in antigen specific manner differentiate into cytotoxic T cells (also referred to as cytotoxic T lymphocytes or CTLs) due to stimulation by the antigen, and then proliferate; this process is referred to herein as "activation" of T cells. Therefore, CTL induction by a certain peptide can be evaluated by presenting the peptide to a T cell by APC, and detecting the induction of CTL. Furthermore, APCs have the effect of activating CD4+ T cells, CD8+ T cells, macrophages, eosinophils and NK cells. Since CD4+ T cells are also important in anti-tumor immunity, the anti-tumor immunity inducing action of the peptide can be evaluated using the activation effect of these cells as indicators.

A method for evaluating the inducing action of CTL using dendritic cells (DCs) as APC is well known in the art. DC is a representative APC having the strongest CTL inducing action among APCs. In this method, the test polypeptide is initially contacted with DC and then this DC is contacted with T cells. Detection of T cells having cytotoxic effects against the cells of interest after the contact with DC shows that the test polypeptide has an activity of inducing the cytotoxic T cells. Activity of CTL against tumors can be detected, for example, using the lysis of $^{51}$Cr-labeled tumor cells as the indicator. Alternatively, it is well known to evaluate the degree of tumor cell damage using ³H-thymidine uptake activity or LDH (lactose dehydrogenase)-release as the indicator.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The test polypeptides confirmed to possess CTL inducing activity by these methods are polypeptides having DC activation effect and subsequent CTL inducing activity. Therefore, polypeptides that induce CTL against tumor cells are useful as vaccines against lung cancer. Furthermore, APC that have acquired the ability to induce CTL against lung cancer by contacting with the polypeptides are useful as vaccines against lung cancer. Furthermore, CTL that have acquired cytotoxicity due to presentation of the polypeptide antigens by APC can be also used as vaccines against lung cancer. Such therapeutic methods for lung cancer, using anti-tumor immunity due to APC and CTL, are referred to as cellular immunotherapy.

Generally, when using a polypeptide for cellular immunotherapy, efficiency of the CTL-induction can be increased by combining a plurality of polypeptides having different structures and contacting them with DC. Therefore, when stimulating DC with protein fragments, it is advantageous to use a mixture of multiple types of fragments.

The induction of anti-tumor immunity by a polypeptide can be further confirmed by observing the induction of antibody production against tumors. For example, when antibodies against a polypeptide are induced in a laboratory animal immunized with the polypeptide, and when growth, proliferation and/or metastasis of tumor cells is suppressed by those antibodies, the polypeptide is determined to induce anti-tumor immunity.

Anti-tumor immunity can be induced by administering a vaccine of this invention, and the induction of anti-tumor immunity enables treatment and prevention of lung cancer. Therapy against or prevention of the onset of lung cancer may include inhibition of the growth of lung cancer cells, involution of lung cancer cells and suppression of occurrence of lung cancer cells. Decrease in mortality of individuals having lung cancer, decrease of lung cancer markers in the blood, alleviation of detectable symptoms accompanying lung cancer and such are also included in the therapy or prevention of lung cancer. Such therapeutic and preventive effects are preferably statistically significant, for example, observed at a significance level of 5% or less, wherein the therapeutic or preventive effect of a vaccine against lung cancer is compared to a control without vaccine administration. For example, Student's t-test, the Mann-Whitney U-test or ANOVA may be used for determining statistical significance.

The above-mentioned peptide, having immunological activity, or a polynucleotide or vector encoding such a peptide, may be combined with an adjuvant. An adjuvant refers to a compound that enhances the immune response against the peptide when administered together (or successively) with the peptide having immunological activity. Examples of suitable adjuvants include cholera toxin, salmonella toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

When using APC or CTL as the vaccine of this invention, lung cancer can be treated or prevented, for example, by the ex vivo method. More specifically, PBMCs of the subject receiving treatment or prevention are collected, contacted ex vivo with a peptide of the present invention. Following the induction of APC or CTL, the cells may be administered to the subject. APC can be also induced by introducing a vector encoding the peptide into PBMCs ex vivo. APC or CTL induced in vitro can be cloned prior to administration. By cloning and growing cells having high activity of damaging target cells, cellular immunotherapy can be performed more effectively. Furthermore, APC and CTL isolated in this manner may be used for cellular immunotherapy not only against individuals from whom the cells are derived, but also against similar types of diseases in other individuals.

Aspects of the present invention are described in the following examples, which are presented only to illustrate the present invention and to assist one of ordinary skill in making and using the same. The examples are not intended in any way to otherwise limit the scope of the invention.

Although methods and materials similar or equivalent to those described herein can be used in the practice or testing of the present invention, suitable methods and materials are described below.

EXAMPLES

The present invention is illustrated, but not restricted, by following Examples.

Materials and Methods

Cell Lines

A24LCL cells (HLA-A24/24) and EHM (HLA-A3/3), human B-lymphoblastoid cell lines, were generous gifts from Takara Shuzo Co, Ltd. (Otsu, Japan). The A24LCL cells were used for peptide-mediated cytotoxicity assays. Lung carcinoma cell lines TE1 (HLA-A2402+), TE13 (HLA-A2402−) and PC9 (HLA-A2402−) were purchased from ATCC. Expression levels of TTK, URLC10 and KOC1 in the lung carcinoma cell lines were determined by cDNA microarray and RT-PCR that revealed strong expression of all three genes in TE1, TTK and KOC1 expression in PC9, and URLC10 expression in TE13 (data not shown).

Candidate Selection of Peptide Derived from TTK, URLC10 and KOC1

9-mer and 10-mer peptides derived from TTK, URLC10 or KOC1 that bind to HLA-A24 molecule were predicted by binding prediction software "BIMAS" (http://bimas.dcrt.nih.gov/cgi-bin/molbio/ken_parker_comboform) (Parker K C, et al., (1994) J Immunol; 152(1):163-75; Kuzushima K, et al., (2001) Blood; 98(6):1872-81). These peptides were synthesized by Mimotopes (San Diego, Calif.) according to the standard solid phase synthesis method and purified by reversed phase HPLC. The purity (>90%) and the identity of the peptides were determined by analytical HPLC and mass spectrometry analysis, respectively. Peptides were dissolved in dimethylsulfoxide (DMSO) at 20 mg/ml and stored at −80° C.

In Vitro CTL Induction

Monocyte-derived dendritic cells (DCs) were used as antigen-presenting cells (APCs) to induce CTL responses against peptides presented on HLA. DCs were generated in vitro as described elsewhere (Nukaya I et al., (1999) Int. J. Cancer 80, 92-7, Tsai V et al., (1997) J. Immunol. 158:1796-802).

Briefly, peripheral blood mononuclear cells (PBMCs) isolated from a normal volunteer (HLA-A*2402) by Ficoll-Paque (Pharmacia) solution were separated by adherence to a plastic tissue culture flask (Becton Dickinson) so as to enrich them for the monocyte fraction. The monocyte-enriched population was cultured in the presence of 1000 U/ml of GM-CSF (provided by Kirin Brewery Company) and 1000 U/ml of IL-4 (Genzyme) in AIM-V (Invitrogen) containing 2% heat-inactivated autologous serum (AS). After 7 days in the culture, the cytokine-generated DCs were pulsed with 20 µg/ml of HLA-A24-binding peptides in the presence of 3 µg/ml of β2-microglobulin for 4 hrs at 20° C. in AIM-V. These peptide-pulsed DCs were then irradiated (5500 rad) and mixed at a 1:20 ratio with autologous $CD8^+$ T cells, obtained by positive selection with Dynabeads M-450 CD8 (Dynal) and DETACHa BEAD™ (Dynal). These cultures were set up in 48-well plates (Corning); each well contained $1.5 \times 10^4$ peptide-pulsed DCs, $3 \times 10^5$ $CD8^+$ T cells and 10 ng/ml of IL-7 (Genzyme) in 0.5 ml of AIM-V/2% AS. Three days later, these cultures were supplemented with IL-2 (CHIRON) to a final concentration of 20 IU/ml. On day 7 and 14, the T cells were further restimulated with the autologous peptide-pulsed DCs. The DCs were prepared each time by the same way described above. Cytotoxicity was tested against peptide-pulsed A24LCL cells after the 3rd round of peptide stimulation on day 21.

CTL Expansion Procedure

CTLs were expanded in culture using the method similar to the one described by Riddell R, et al., (Walter E A et al., (1995) N Engl J Med 333:1038-44; Riddel et al., (1996) Nature Med. 2:216-23). A total $5 \times 10^4$ of CTLs were resuspended in 25 ml of AIM-V/5% AS with $25 \times 10^6$ irradiated (3300 rad) PBMC and $5 \times 10^6$ irradiated (8000 rad) EHM cells in the presence of 40 ng/ml of anti-CD3 monoclonal antibody (Pharmingen). One day after initiating the cultures, 120 IU/ml of IL-2 were added to the cultures. The cultures were fed with fresh AIM-V/5% AS containing 30 IU/ml of IL-2 on days 5, 8 and 11.

Establishment of CTL Clones

The dilutions were made to have 0.3, 1, and 3 CTLs/well in 96 round-bottomed micro titer plate (Nalge Nunc International). CTLs were cultured with $7 \times 10^4$ cells/well of allogenic PBMCs, $1 \times 10^4$ cells/well of EHM, 30 ng/ml of anti-CD3 antibody, and 125 U/ml of IL-2 in total of 150 µl/well of AIM-V containing 5% AS. 50 µl/well of IL-2 was added to the medium 10 days later so that IL-2 became 125 U/ml in the final concentration. Cytotoxic activity of CTLs was tested on the 14th day, and CTL clones were expanded using the same method above.

Cytotoxicity Assay

Target cells were labeled with 100 µCi of $Na_2{}^{51}CrO_4$ for 1 hr at 37° C. in a $CO_2$ incubator (Perkin Elmer Life Sciences). Peptide-pulsed targets were prepared by incubating the cells with 20 µg/ml of the peptide for 16 hrs at 37° C. before labeling. Labeled target cells were rinsed and mixed with effector cells in a final volume of 0.2 ml in round-bottom microtiter plates. The plates were centrifuged (4 minutes at 800×g) to increase cell-to-cell contact and placed in a $CO_2$ incubator at 37° C. After 4 hrs of incubation, 0.1 ml of the supernatant was collected from each well and the radioactivity was determined with a gamma counter.

The percentage of specific cytotoxicity was determined by calculating the percentage of specific $^{51}$Cr-release by the following formula:

{(cpm of the test sample release−cpm of the spontaneous release)/(cpm of the maximum release−cpm of the spontaneous release)}×100.

Spontaneous release was determined by incubating the target cells alone, in the absence of effector cells, and the maximum release was obtained by incubating the target cells with 1N HCl. All measurements were done in duplicate, and the standard errors of the means were consistently below 10% of the value of the mean.

Antigen specificity was confirmed by the cold target inhibition assay, which utilized unlabeled A24LCL cells that were pulsed with or without peptide (20 µg/ml for 16 hrs at 37° C.) to compete for the recognition of $^{51}$Cr-labeled tumor cells.

Blocking assay of cytotoxicity using the monoclonal antibodies (mAbs) (mouse anti-MHC-class I mAb, anti-MHC-class II mAb, anti-CD8 mAb, and anti-CD4 mAb) was performed to confirm the HLA restriction manner. Anti-mouse IgG1, anti-mouse IgG2a mAbs were used as Isotype.

Results

Prediction of HLA-A24 Binding Peptides Derived from TTK, URLC10 or KOC1

Table 1 shows the HLA-A*2402 binding peptides for TTK (GenBank Accession No. NM_003318; SEQ ID Nos.1, 2) in order of binding affinity. Table 1A shows 9-mer peptides derived from TTK and Table 1B shows 10-mer peptides derived from TTK. Table 2 shows the HLA-A*2402 binding peptides for URLC10 (GenBank Accession No. AB105187; SEQ ID Nos.3, 4) in order of binding affinity. Table 2A shows 9-mer peptides derived from URLC10 and Table 2B shows 10-mer peptides derived from URLC10. Table 3 shows the HLA-A*2402 binding peptides for KOC1 (GenBank Accession No. NM_006547; SEQ ID Nos.5, 6) in order of binding affinity. Table 3A shows 9-mer peptides derived from KOC1 and Table 3B shows 10-mer peptides derived from KOC1.

TABLE 1A

HLA-A24 binding 9-mer peptides derived from TTK

| Start Position | Amino Acid Sequence | SEQ ID No. | Binding Score | Start Position | Amino Acid Sequence | SEQ ID No. | Binding Score | |
|---|---|---|---|---|---|---|---|---|
| 90 | RYSQAIEAL | 7 | 400 | 71 | KLEKNSVPL | 17 | 12 | |
| 567 | SYRNEIAYL | 8 | 200 | 201 | KNLSASTVL | 18 | 12 | N.D |
| 549 | IYAIKYVNL | 9 | 200 | 467 | RTPVVKNDF | 19 | 10.1 | N.D |
| 590 | DYEITDQYI | 10 | 90 | 102 | KYGQNESFA | 20 | 10 | N.D |

TABLE 1A-continued

HLA-A24 binding 9-mer peptides derived from TTK

| Start Position | Amino Acid Sequence | SEQ ID No. | Binding Score | Start Position | Amino Acid Sequence | SEQ ID No. | Binding Score | |
|---|---|---|---|---|---|---|---|---|
| 652 | NFLIVDGML | 11 | 42 | 19 | KVRDIKNKF | 21 | 8.9 | N.D |
| 141 | KFAFVHISF | 12 | 28 | 777 | KQRISIPEL | 22 | 8.8 | N.D |
| 214 | SFSGSLGHL | 13 | 20 | 75 | NSVPLSDAL | 23 | 8.6 | N.D |
| 28 | KNEDLTDEL | 14 | 19 | 605 | GNIDLNSWL | 24 | 8.6 | N.D |
| 111 | RIQVREAEL | 15 | 15.8 | 596 | QYIYMVMEC | 25 | 8.3 | N.D |
| 108 | SFARIQVRF | 16 | 14 | 535 | GSSKVFQVL | 26 | 8.1 | N.D |

Start position indicates the number of amino acid from N-terminal of TTK. Binding score is derived from "BIMAS" described in Materials and Methods.
N.D. indicates "not done"

TABLE 1B

HLA-A24 binding 10-mer peptides derived from TTK

| Start Position | Amino Acid Sequence | SEQ ID No. | Binding Score | Start Position | Amino Acid Sequence | SEQ ID No. | Binding Score |
|---|---|---|---|---|---|---|---|
| 810 | KYVLGQLVGL | 27 | 600 | 168 | KAVERGAVPL | 37 | 14.4 |
| 725 | YYMTYGKTPF | 28 | 150 | 232 | RGQTTKARFL | 38 | 12 |
| 598 | IYMVMECGNI | 29 | 75 | 185 | RNLNLQKKQL | 39 | 12 |
| 728 | TYGKTPFQQI | 30 | 72 | 777 | KQRISIPELL | 40 | 11.2 |
| 755 | EFPDIPEKDL | 31 | 36 | 573 | AYLNKLQQHS | 41 | 10.8 |
| 490 | CFQQQQHQIL | 32 | 36 | 373 | EYQEPEVPES | 42 | 9.9 |
| 143 | AFVHISFAQF | 33 | 18 | 74 | KNSVPLSDAL | 43 | 9.6 |
| 569 | RNEIAYLNKL | 34 | 15.8 | 315 | KPSGNDSCEL | 44 | 8.8 |
| 359 | KTESSLLAKL | 35 | 15.8 | 61 | NPEDWLSLLL | 45 | 8.6 |
| 553 | KYVNLEEADN | 36 | 15 | 763 | DLQDVLKCCL | 46 | 8.6 |

Start position indicates the number of amino acid from N-terminal of TTK. Binding score is derived from "BIMAS" described in Materials and Methods.

TABLE 2A

HLA-A24 binding 9-mer peptides derived from URLC10

| Start Position | Amino Acid Sequence | SEQ ID No. | Binding Score | Start Position | Amino Acid Sequence | SEQ ID No. | Binding Score | |
|---|---|---|---|---|---|---|---|---|
| 154 | KPEEKRFLL | 47 | 14.4 | 193 | EYAGSMGES | 57 | 5.5 | N.D |
| 48 | RADPPWAPL | 48 | 9.6 | 168 | FFYLKCCKI | 58 | 5.5 | N.D |
| 205 | LWLAILLLL | 49 | 8.4 | 128 | AAVKIFPRF | 59 | 5 | N.D |
| 57 | GTMALLALL | 50 | 7.2 | 58 | TMALLALLL | 60 | 4.8 | N.D |
| 203 | GGLWLAILL | 51 | 7.2 | 152 | RPKPEEKRF | 61 | 4.8 | N.D |
| 62 | LALLLVVAL | 52 | 7.2 | 197 | SMGESCGGL | 62 | 4.8 | N.D |
| 53 | WAPLGTMAL | 53 | 6 | 173 | CCKIRYCNL | 63 | 4 | N.D |
| 214 | ASIAAGLSL | 54 | 6 | 28 | DPGRGARRL | 64 | 4 | N.D |

TABLE 2A-continued

HLA-A24 binding 9-mer peptides derived from URLC10

| Start Position | Amino Acid Sequence | SEQ ID No. | Binding Score | | Start Position | Amino Acid Sequence | SEQ ID No. | Binding Score | |
|---|---|---|---|---|---|---|---|---|---|
| 54 | APLGTMALL | 55 | 6 | | 31 | RGARRLRRF | 65 | 4 | N.D |
| 212 | LLASIAAGL | 56 | 5.6 | N.D | 202 | CGGLWLAIL | 66 | 4 | N.D |

Start position indicates the number of amino acid from N-terminal of URLC10.
Binding score is derived from "BIMAS" described in Materials and Methods.
N.D. indicates "not done"

TABLE 2B

HLA-A24 binding 10-mer peptides derived from URLC10

| Start Position | Amino Acid Sequence | SEQ ID No. | Binding Score | | Start Position | Amino Acid Sequence | SEQ ID No. | Binding Score | |
|---|---|---|---|---|---|---|---|---|---|
| 177 | RYCNLEGPPI | 67 | 100 | | 196 | GSMGESCGGL | 77 | 6 | N.D |
| 159 | RFLLEEPMPF | 68 | 30 | | 204 | GLWLAILLLL | 78 | 5.6 | N.D |
| 152 | RPKPEEKRFL | 69 | 9.6 | | 123 | PYCVIAAVKI | 79 | 5.5 | N.D |
| 211 | LLLASIAAGL | 70 | 8.4 | | 193 | EYAGSMGESC | 80 | 5 | N.D |
| 172 | KCCKIRYCNL | 71 | 8 | | 61 | LLALLLVVAL | 81 | 4.8 | N.S |
| 169 | FYLKCCKIRY | 72 | 7.5 | | 202 | CGGLWLAILL | 82 | 4.8 | N.D |
| 57 | GTMALLALLL | 73 | 7.2 | | 56 | LGTMALLALL | 83 | 4.8 | N.D |
| 53 | WAPLGTMALL | 74 | 6 | | 70 | LPRVWTDANL | 84 | 4 | N.D |
| 203 | GGLWLAILLL | 75 | 6 | N.D | 201 | SCGGLWLAIL | 85 | 4 | N.D |
| 198 | MGESCGGLWL | 76 | 6 | N.D | 213 | LASIAAGLSL | 86 | 4 | N.D |

Start position indicates the number of amino acid from N-terminal of URLC10.
Binding score is derived from "BIMAS" described as Materials and Methods.
N.D. indicates "not done".
N.S. indicates "not synthesized"

TABLE 3A

HLA-A24 binding 9-mer peptides derived from KOC1

| Start Position | Amino Acid Sequence | SEQ ID No. | Binding Score | Start Position | Amino Acid Sequence | SEQ ID No. | Binding Score | |
|---|---|---|---|---|---|---|---|---|
| 350 | SYENDIASM | 87 | 37.5 | 4 | LYIGNLSEN | 97 | 8.25 | |
| 141 | GFQLENFTL | 88 | 30 | 423 | KQGQHIKQL | 98 | 8 | N.D |
| 508 | KTVNELQNL | 89 | 14.4 | 561 | KQHQQQKAL | 99 | 8 | N.D |
| 26 | KIPVSGPFL | 90 | 12 | 310 | ITISPLQEL | 100 | 7.9 | N.D |
| 192 | KPCDLPLRL | 91 | 11.5 | 470 | IYGKIKEEN | 101 | 7.7 | N.D |
| 433 | RFAGASIKI | 92 | 11 | 356 | ASMNLQAHL | 102 | 7.2 | N.D |
| 505 | KGGKTVNEL | 93 | 10.6 | 93 | QWEVLDSLL | 103 | 7.2 | N.D |
| 190 | KQKPCDLPL | 94 | 9.6 | 43 | DCPDESWAL | 104 | 7.2 | N.D |
| 152 | AYIPDEMAA | 95 | 9 | 92 | LQWEVLDSL | 105 | 6.7 | N.D |
| 320 | LYNPERTIT | 96 | 9 | 55 | EALSGKIEL | 106 | 6.6 | N.D |

Start position indicates the number of amino acid from N-terminal of KOC1.
Binding score is derived from "BIMAS" described in Materials and Methods.
N.D. indicates "not done"

TABLE 3B

HLA-A24 binding 10-mer peptides derived from KOC1

| Start Position | Amino Acid Sequence | SEQ ID No. | Binding Score | | Start Position | Amino Acid Sequence | SEQ ID No. | Binding Score | |
|---|---|---|---|---|---|---|---|---|---|
| 470 | IYGKIKEENF | 107 | 100 | | 91 | HLQWEVLDSL | 117 | 8.4 | N.D |
| 272 | KFTEEIPLKI | 108 | 18.5 | | 359 | NLQAHLIPGL | 118 | 7.2 | N.D |
| 290 | RLIGKEGRNL | 109 | 12 | | 364 | LIPGLNLNAL | 119 | 7.2 | N.D |
| 309 | KITISPLQEL | 110 | 10.6 | | 165 | LQQPRGRRGL | 120 | 7.2 | N.D |
| 350 | SYENDIASMN | 111 | 10.5 | | 273 | FTEEIPLKIL | 121 | 7.2 | N.D |
| 192 | KPCDLPLRLL | 112 | 9.6 | | 406 | ETVHLFIPAL | 122 | 6 | N.D |
| 320 | LYNPERTITV | 113 | 9 | N.D | 138 | KLNGFQLENF | 123 | 6 | N.D |
| 4 | LYIGNLSENA | 114 | 9 | N.D | 9 | LSENAAPSDL | 124 | 6 | N.D |
| 548 | VAQRKIQEIL | 115 | 8.4 | N.D | 88 | IPPHLQWEVL | 125 | 6 | N.D |
| 83 | LQIRNIPPHL | 116 | 8.4 | N.D | 127 | SSKDQARQAL | 126 | 5.7 | N.D |

Start position indicates the number of amino acid from N-terminal of KOC1.
Binding score is derived from "BIMAS" described in Materials and Methods.
N.D. indicates "not done"

Stimulation of the T Cells Using the Predicted Peptides

CTLs for those peptides derived from TTK, URLC10 or KOC1 were generated in the manner described in "Materials and Methods" section above. Resulting CTLs showing detectable cytotoxic activity were expanded, and those CTL clones that demonstrated higher cytotoxic activities against the peptide-pulsed target as compared to the activities against target without peptide pulse were established.

The CTL clones stimulated by the HLA-A24 binding peptides TTK-567 (SYRNEIAYL (SEQ ID No.8)) (FIG. 1), URLC10-177 (RYCNLEGPPI (SEQ ID No.67)) (FIG. 2) or by KOC1-508 (KTVNELQNL (SEQ ID No.89)) (FIG. 3) showed potent cytotoxic activity against the peptide-pulsed target without showing any significant cytotoxic activity against targets not pulsed with any peptide.

Cytotoxic Activity Against Lung Cancer Cell Lines Endogenously Expressing TTK, URLC10 or KOC1

Figure 4:
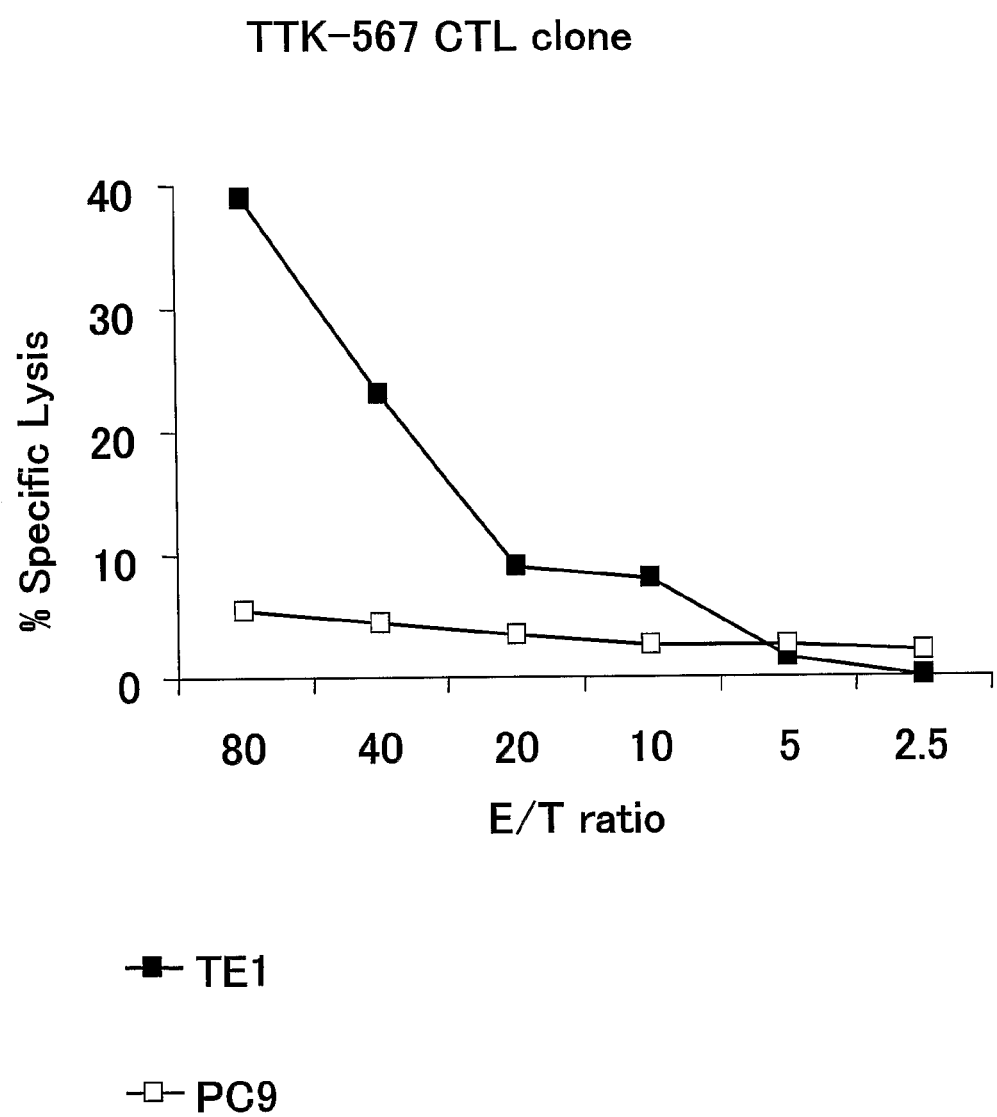
FIG. 4 is a graph showing that the CTL clone raised by TTK-567 recognizes and lyses tumor cells endogenously expressing TTK in an HLA restricted fashion. Cytotoxic activity against TE1 cells, which endogenously express TTK and HLA-A24, was tested using as effector cells the CTL clones raised by TTK-567. PC9 cells were used as the target cells that endogenously express TTK but do not express HLA-A24. The CTL clone showed high cytotoxic activity against TE1 cells that express both TTK and HLA-A24. On the other hand, it did not show significant cytotoxic activity against PC9 cells that express TTK but not HLA-A24.
Figure 5:
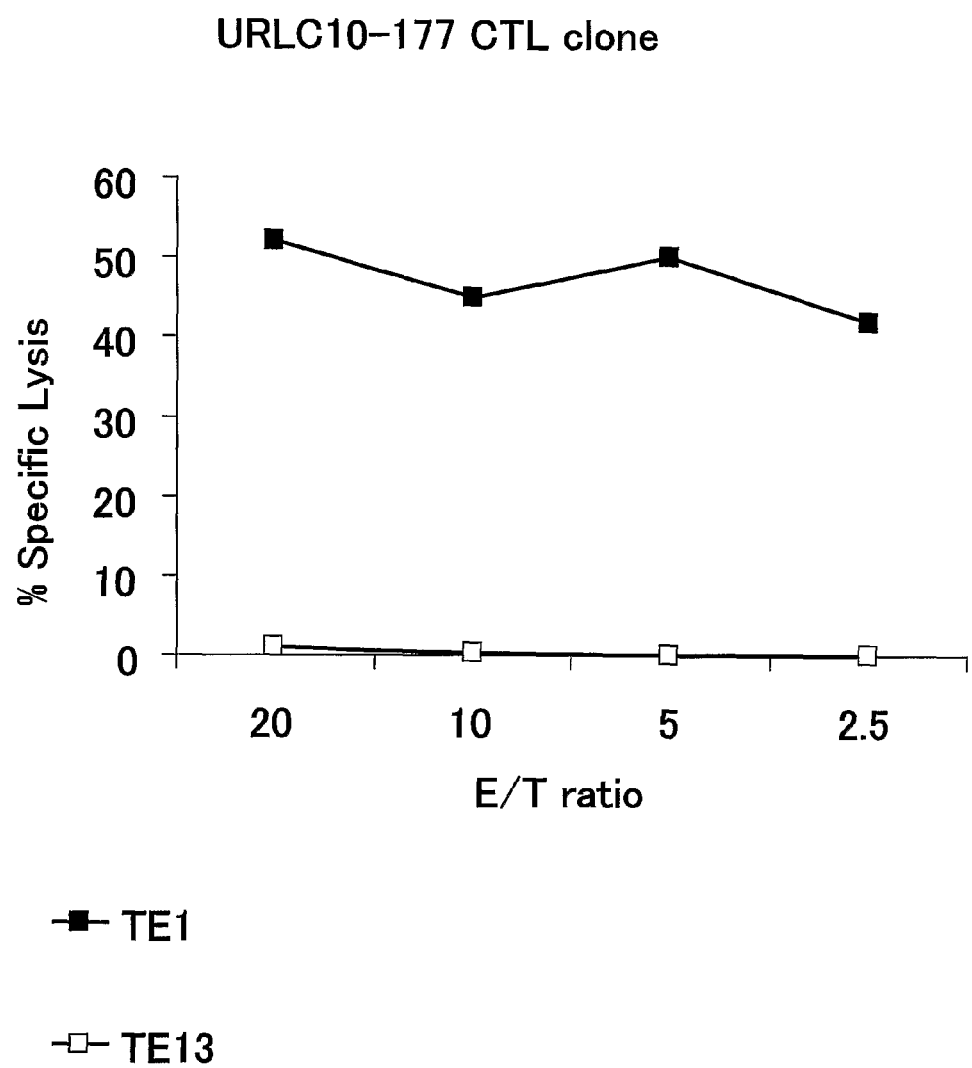
FIG. 5 is a graph showing that the CTL clone raised by URLC10-177 recognizes and lyses tumor cells endogenously expressing URLC10 in an HLA restricted fashion. Cytotoxic activity against TE1 cells, which endogenously express URLC10 and HLA-A24, was tested using as effector cells the CTL clone raised by URLC10-177. TE13 cells were used as the target cells that endogenously express URLC10 but do not express HLA-A24. The CTL clone showed high cytotoxic activity against TE1 cells that express both URLC10 and HLA-A24. On the other hand, it did not show significant cytotoxic activity against TE13 cells that express URLC10, but not HLA-A24.
Figure 6:
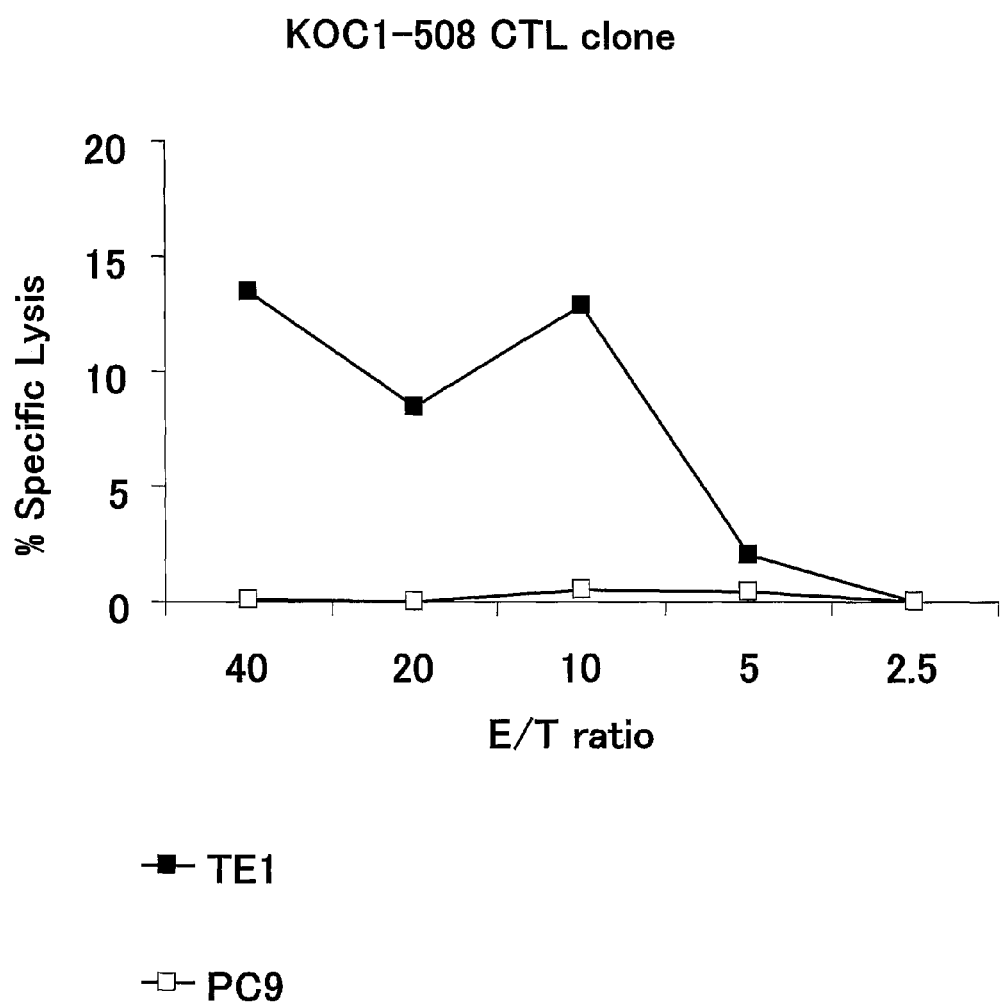
FIG. 6 is a graph showing that the CTL clone raised by KOC1-508 recognizes and lyses the tumor cells endogenously expressing KOC1 in an HLA restricted fashion. Cytotoxic activity against TE1 cells, which endogenously express KOC1 and HLA-A24, was tested using as effector cells the CTL clone raised by KOC1-508. PC9 cells were used as the target cells that endogenously express KOC1 but do not express HLA-A24. The CTL clone showed high cytotoxic activity against TE1 cells that express both KOC1 and HLA-A24. On the other hand, it did not show significant cytotoxic activity against PC9 cells that express KOC1, but not HLA-A24.

The established CTL clones described above were examined for their ability to recognize and kill tumor cells endogenously expressing TTK, URLC10 or KOC1. Cytotoxic activity against TE1 cells, which endogenously express TTK and HLA-4, was tested using as effector cells the CTL clone raised by TTK-567. PC9 cells were used as the target cells that endogenously express TTK but not HLA-A24. The CTL clone showed high cytotoxic activity against the TE1 cells that express both TTK and HLA-4. On the other hand, it did not show significant cytotoxic activity against the PC9 cells that express TTK but not HLA-A24 (FIG. 4). Cytotoxic activity against TE1 cells, which endogenously express URLC10 and HLA-A24, was tested using as effector cells the CTL clone raised by URLC10-177. TE13 cells were used as the target cells that endogenously express URLC10 but not HLA-A24. The CTL clone showed high cytotoxic activity against the TE1 cells that express both URLC10 and HLA-A24. On the other hand, it did not show significant cytotoxic activity against the TE13 cells that express URLC10 but not HLA-A24 (FIG. 5). Cytotoxic activity against TE1 cells, which endogenously express KOC1 and HLA-A24, was tested using as effector cells the CTL clone raised by KOC1-508. PC9 cells were used as the target cells that endogenously express KOC1 but not HLA-A24. The CTL clone showed high cytotoxic activity against the TE1 cells that express both KOC1, and HLA-A24. On the other hand, it did not show significant cytotoxic activity against the PC9 cells that express KOC1 but not HLA-A24 (FIG. 6).

Figure 2:
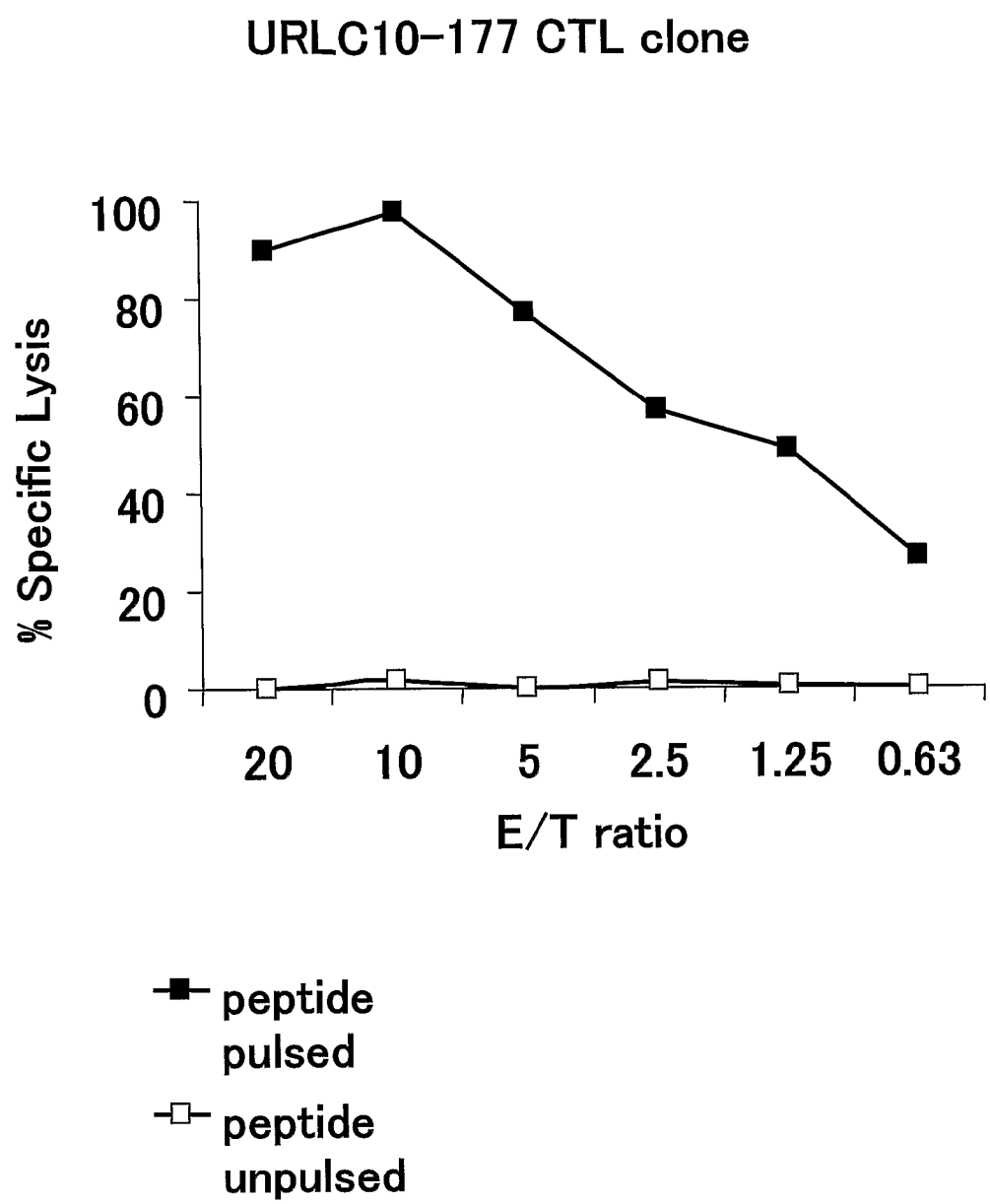
FIG. 2 is a graph showing that the CTL clone raised by URLC10-177 has peptide-specific cytotoxicity. Specifically, the CTL clone showed high cytotoxic activity against target cells (A24LCL) pulsed with URLC10-177, whereas it did not show significant cytotoxic activity against the same target cells (A24LCL) pulsed with no peptides.
Figure 3:
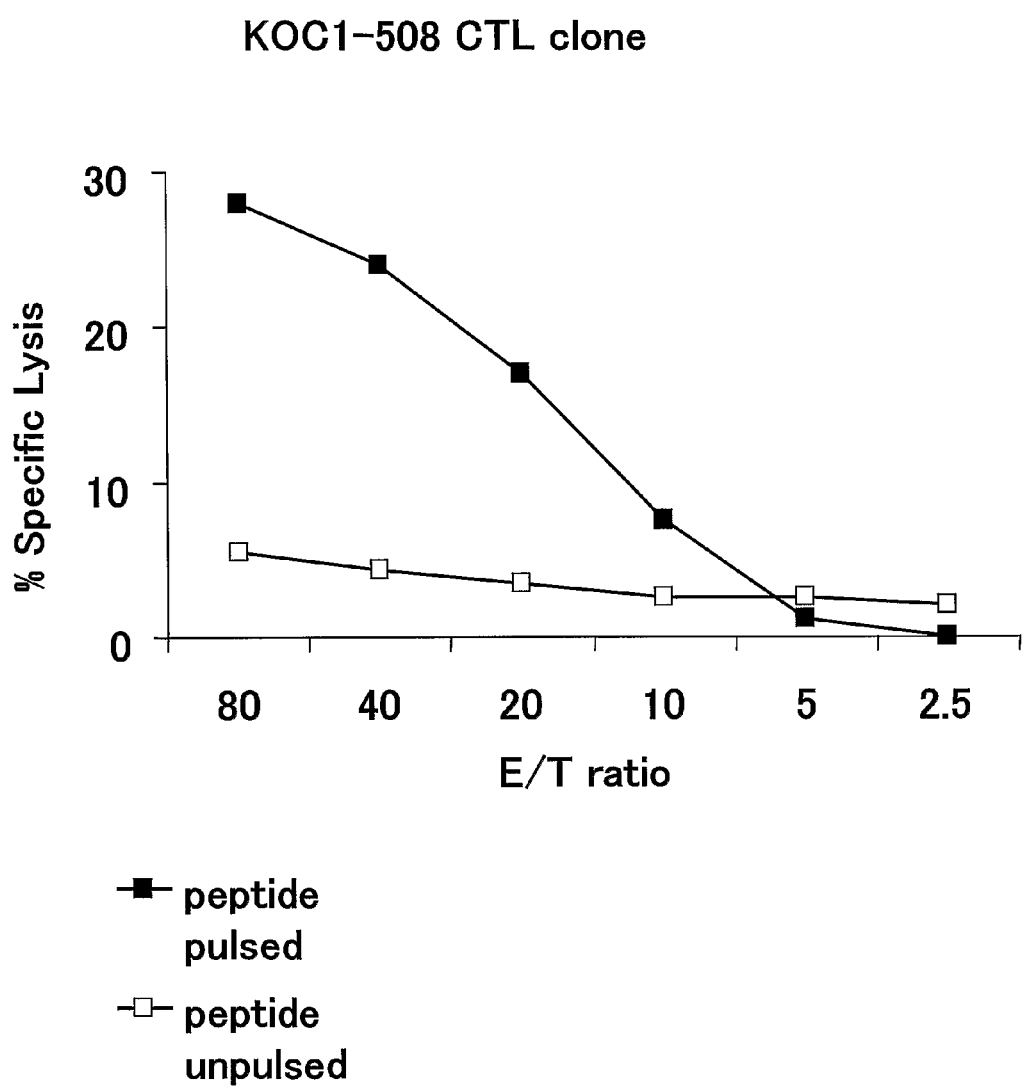
FIG. 3 is a graph showing that the CTL clone raised by KOC1-508 has peptide-specific cytotoxicity. Specifically, the CTL clone showed high cytotoxic activity against target cells (A24LCL) pulsed with KOC1-508, whereas it did not show significant cytotoxic activity against the same target cells (A24LCL) pulsed with no peptides.

The above-described CTL clones showed potent cytotoxic activity against the TE1 lung cancer cell line, a cell line that expresses TTK, URLC10 and KOC1, and HLA-A24. On the other hand, the CTL clones against TTK-567 or KOC1-508 showed no cytotoxic activity against the PC9 lung cancer cell line, a cell line that expresses TTK and KOC1 but not HLA-A24; likewise, the CTL clone raised against URLC10-177 did not show a cytotoxic activity against the TE13 lung cancer cell line, a cell line that expresses URLC10 but not HLA-A24. These CTL clones also show no cytotoxic activity against A24LCL cells, cell that express HLA-A24, but do not express TTK, URLC10 or KOC1 (FIGS. 1, 2 and 3). These results clearly demonstrate that TTK-567, URLC10-177 and KOC1-508 were naturally expressed to the tumor cell surface with HLA-A4 molecule and recognized CTL.

Cold Target Inhibition Assay

Figure 7:
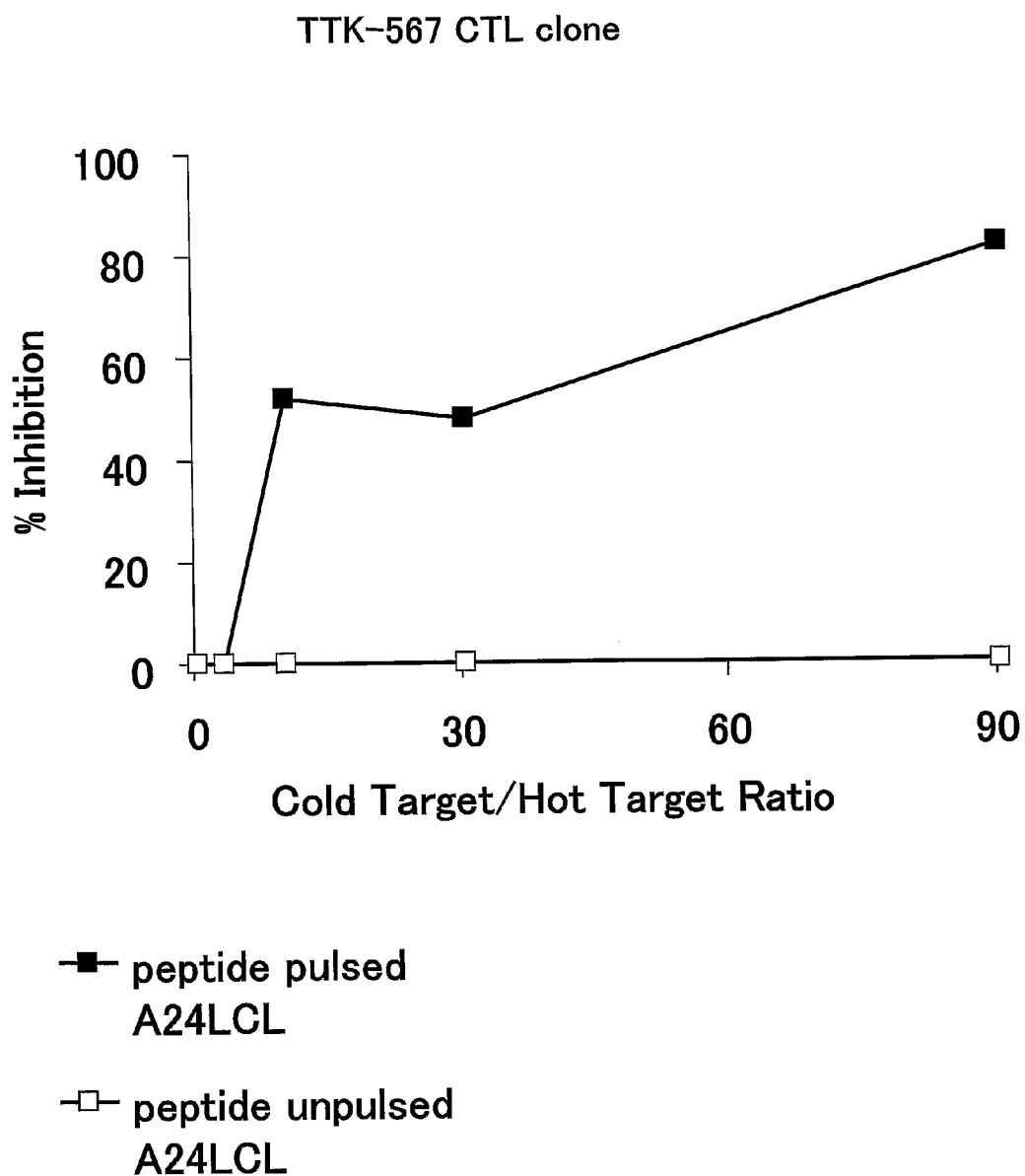
FIG. 7 is a graph showing that the CTL clone raised by TTK-567 specifically recognizes TTK-567 in an HLA-A24 restricted manner. TE1 cells labeled by $Na_2{}^{51}CrO_4$ were prepared as hot target, while TTK-567 peptide-pulsed A24LCL cells were used as cold target (Inhibitor). The E/T ratio was fixed at 20. The cytotoxic activity of TTK-567 CTL clone against TE1 cells was inhibited by the addition of A24LCL cells pulsed with the identical peptide.
Figure 8:
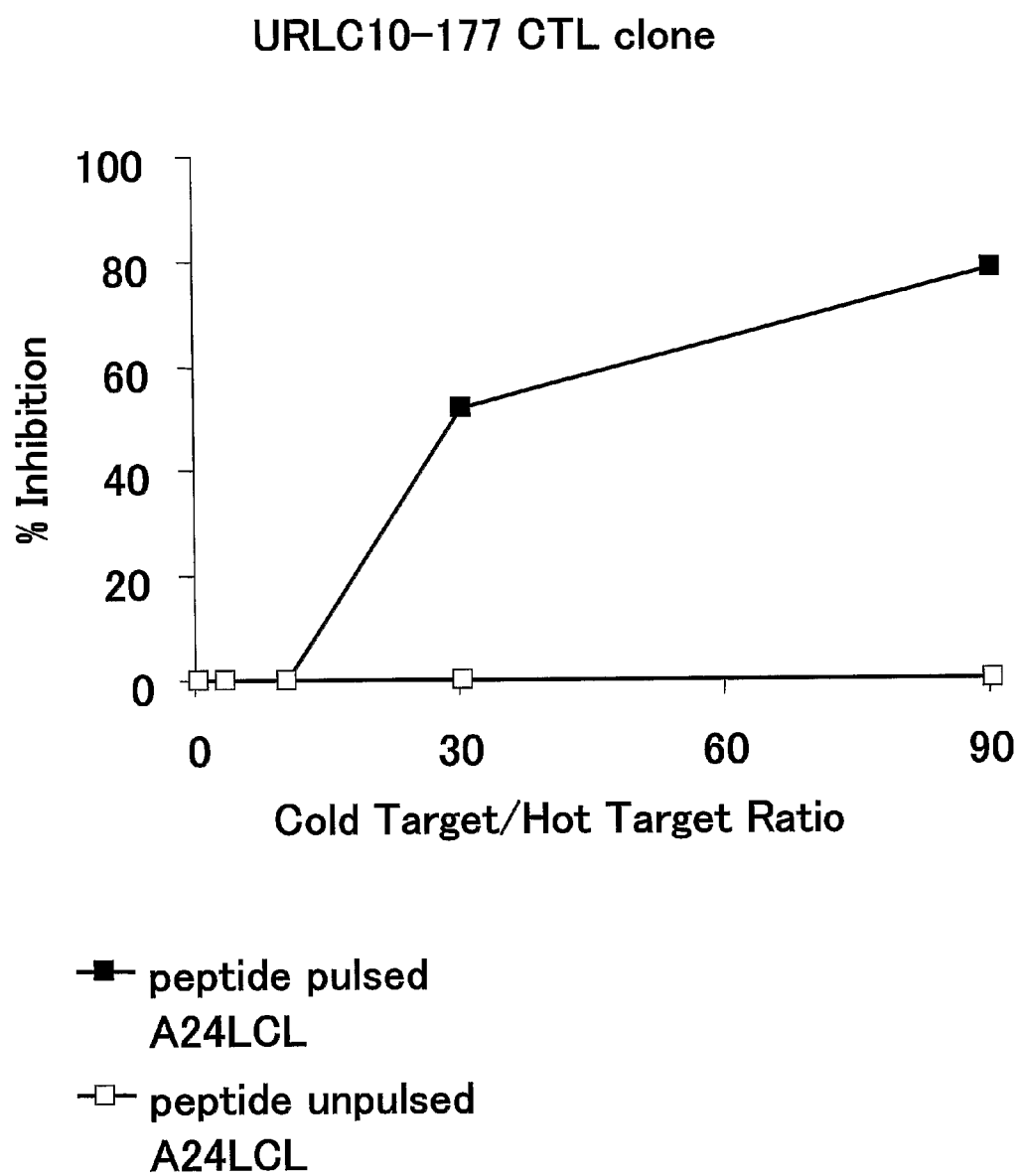
FIG. 8 is a graph showing that the CTL clone raised by URLC10-177 specifically recognizes URLC10 in an HLA-A24 restricted manner. TE1 cells labeled by $Na_2{}^{51}CrO_4$ were prepared as hot target, while URLC10-177 peptide-pulsed A24LCL cells were used as cold target (Inhibitor). The E/T ratio was fixed at 20. The cytotoxic activity of URLC10-177 CTL clone against TE1 was inhibited by the addition of A24LCL cells pulsed with the identical peptide.
Figure 9:
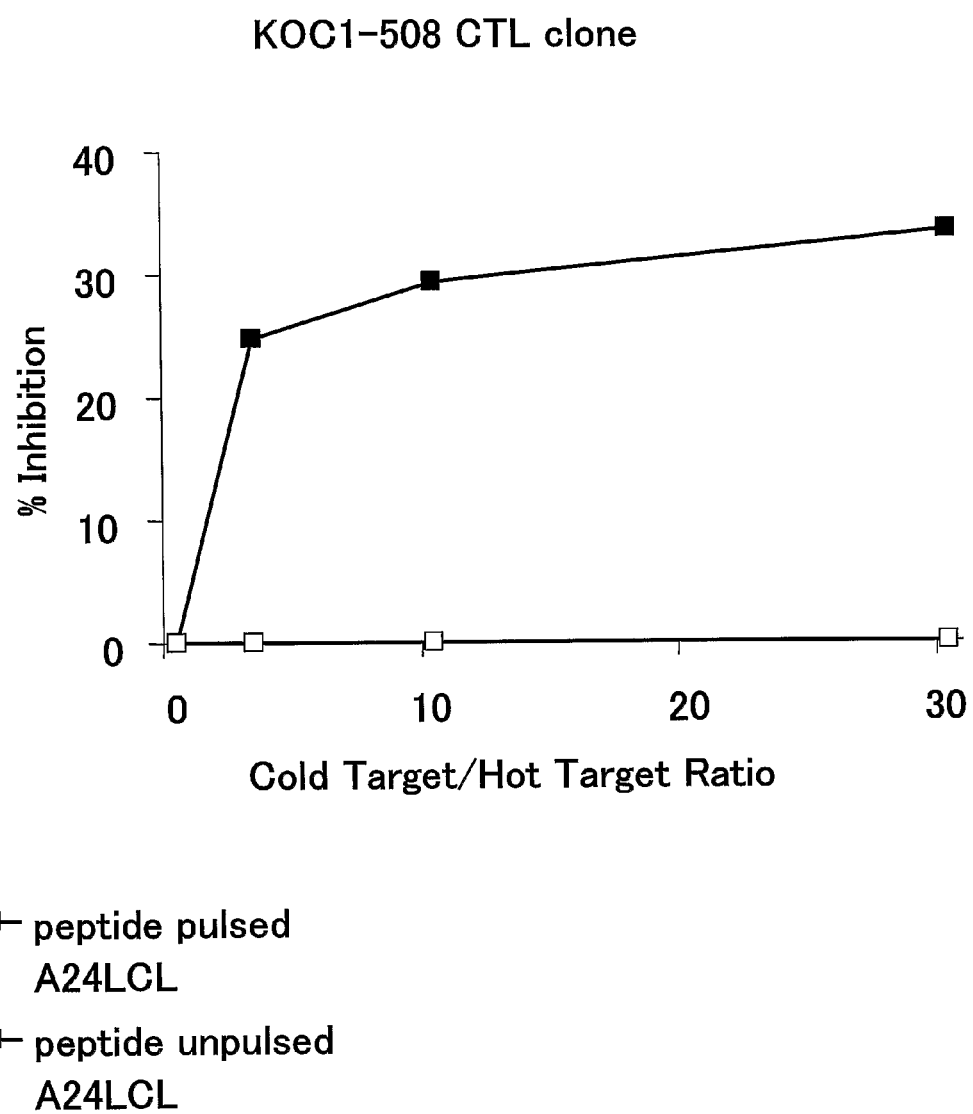
FIG. 9 is a graph showing that the CTL clone raised by KOC1-508 specifically recognizes KOC1 in an HLA-A24 restricted manner. TE1 cells labeled by $Na_2{}^{51}CrO_4$ were prepared as hot target, while KOC1-508 peptide-pulsed A24LCL cells were used as cold target (Inhibitor). The E/T ratio was fixed at 20. The cytotoxic activity of KOC1-508 CTL clone against TE1 cells was inhibited by the addition of A24LCL cells pulsed with the identical peptide.

Cold target inhibition assay was performed to confirm the specificity of the CTL clones as described in "Materials and Methods" section above. TE1 cells labeled by $Na_2^{51}CrO_4$ were prepared as hot target, while TTK-567 peptide-pulsed A24LCL cells were used as cold target (Inhibitor). The cytotoxic activity of the TTK-567 CTL clone against TE1 cells was specifically inhibited by the addition of 4LCL cells pulsed with the identical peptide (FIG. 7). Regarding URLC10, TE1 cells labeled by $Na_2^{51}CrO_4$ were prepared as hot target, while URLC10-177 peptide-pulsed A24LCL cells were used as cold target (Inhibitor). The cytotoxic activity of the URLC10-177 CTL clone against TE1 was specifically inhibited by the addition of A24LCL cells pulsed with the identical peptide (FIG. 8). As above, TE1 cells labeled by $Na_2^{51}CrO_4$ were prepared as hot target, while KOC1-508 peptide-pulsed A24LCL cells were used as cold target (Inhibitor). The E/T ratio was fixed at 20. The cytotoxic activity of KOC1-508 CTL clone against TE1 cells was specifically inhibited by the addition of A24LCL cells pulsed with the identical peptide (FIG. 9). Specific cytotoxicity against target TE1 cells was significantly inhibited when peptide-pulsed cold target was added in the assay at various ratios but not inhibited at all by the addition of cold target. These results were indicated as a percentage of specific lysis inhibition at the E/T ratio of 20.

Blocking of CTL Activity by Antibodies that Bind to T-Cell Surface Antigens

Figure 10:
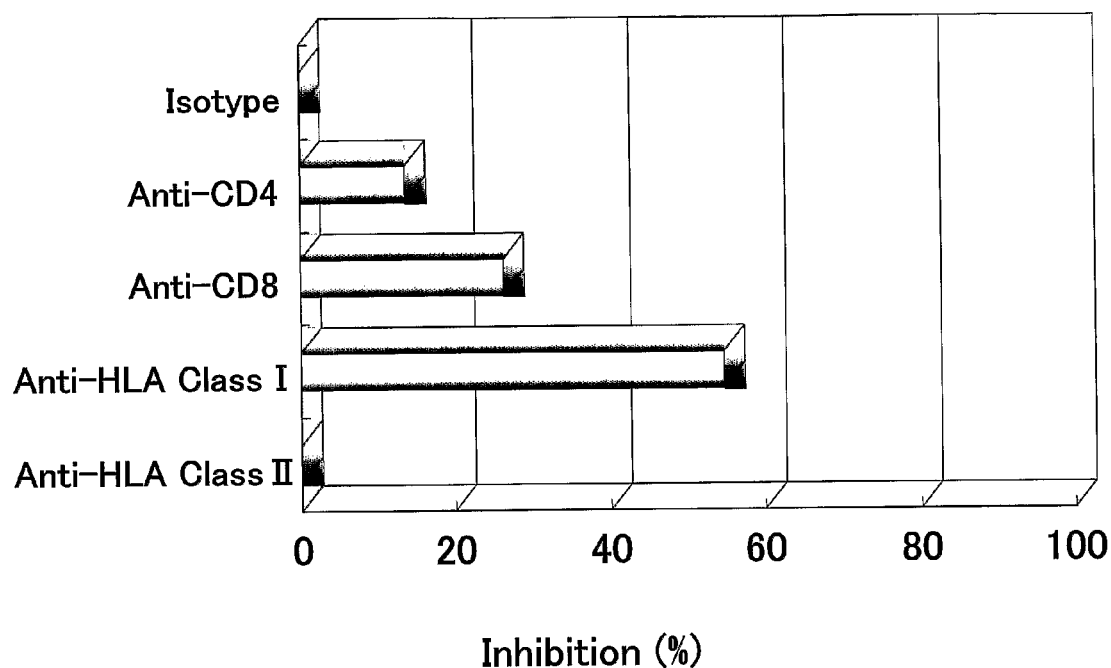
FIG. 10 is a graph showing that the cytotoxic activity of the CTL clone raised by TTK-567 is specifically blocked by antibodies recognizing the T-cell surface antigens of HLA class I or CD8. The specificity of cytotoxicity of the CTL clone was confirmed by an antibody blocking assay. TE1 cells were co-cultured with monoclonal antibodies respectively, and used as a target. The CTL activity was clearly blocked the addition of antibodies that recognize HLA Class I or CD8 and was marginally affected the addition of antibodies to HLA Class II or CD4; however, it was not inhibited at all by the addition of an isotype-matched control antibody.
Figure 11:
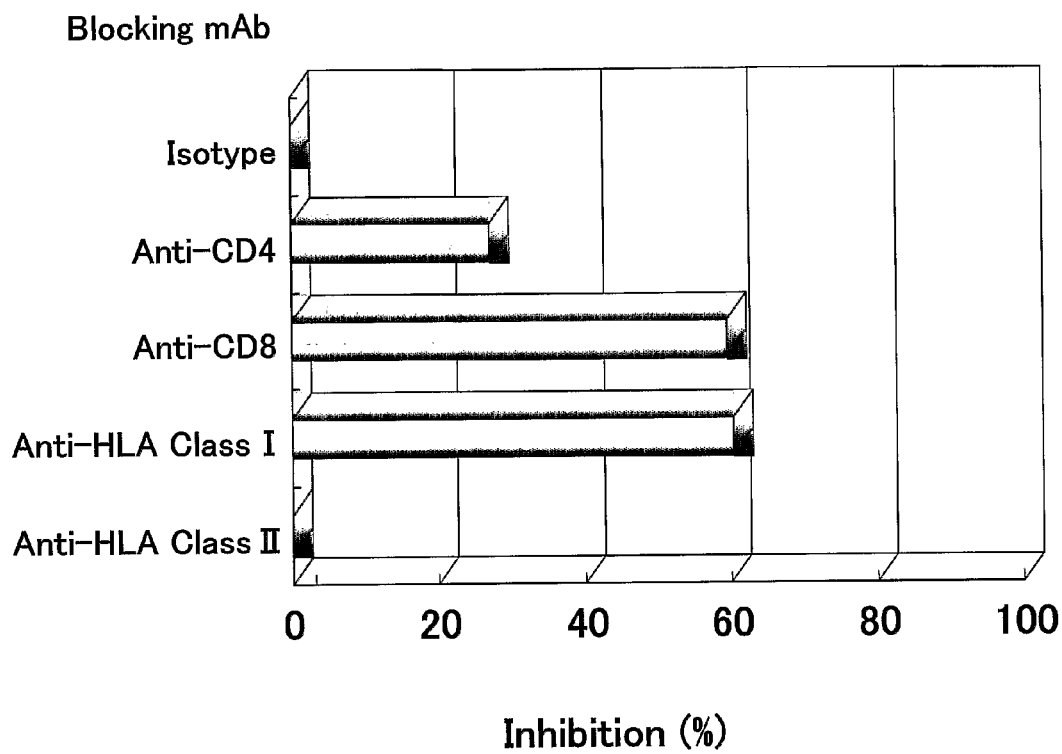
FIG. 11 is a graph showing that the cytotoxic activity of the CTL clone raised by URLC10-177 is specifically blocked by antibodies recognizing the T-cell surface antigens of HLA class I or CD8. The specificity of cytotoxicity of the CTL clone was confirmed by an antibody blocking assay. TE1 cells were co-cultured with monoclonal antibodies respectively, and used as a target. The CTL activity was clearly blocked by the addition of antibodies that recognize HLA Class I or CD8 and was marginally affected by the addition of antibodies to HLA Class II or CD4; however, it was not inhibited at all by the addition of an isotype-matched control antibody.
Figure 12:
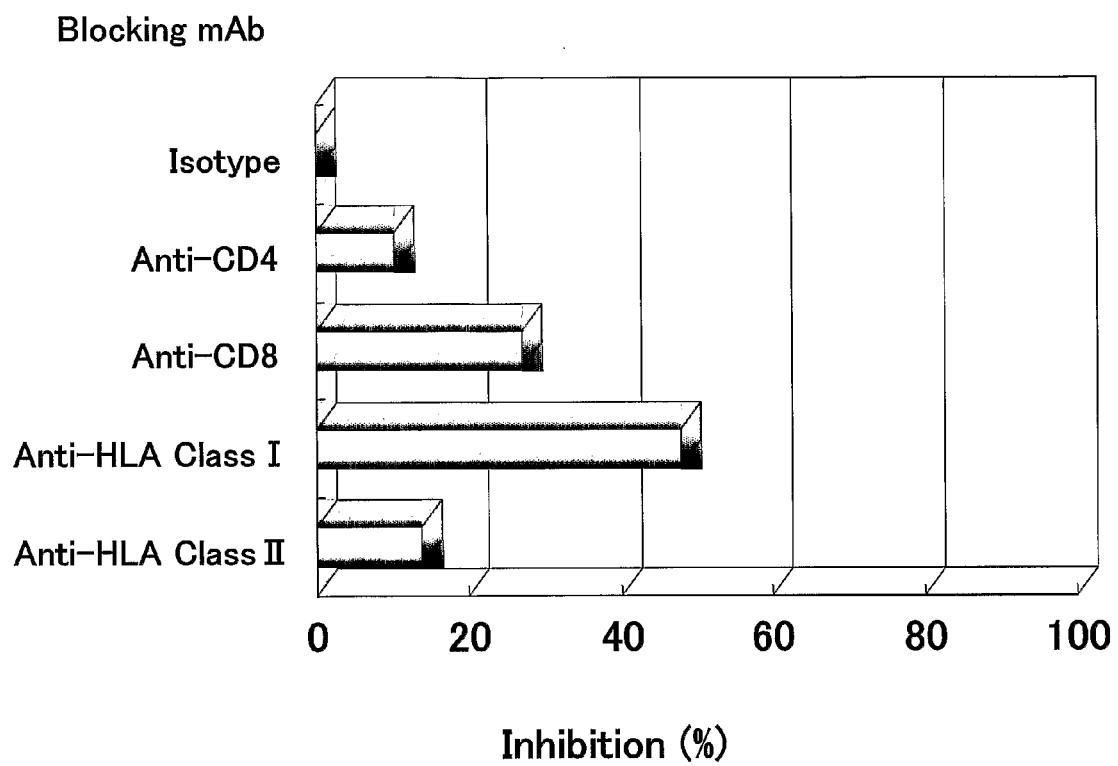
FIG. 12 is a graph showing that the cytotoxic activity of the CTL clone raised by KOC1-508 is specifically blocked by antibodies recognizing the T-cell surface antigens of HLA class I or CD8. The specificity of cytotoxicity of the CTL clone was confirmed by an antibody blocking assay. TE1 cells were co-cultured with monoclonal antibodies respectively, and used as a target. The CTL activity was clearly blocked by the addition of antibodies that recognize HLA Class I or CD8 and was marginally affected by the addition of antibodies to HLA Class II or CD4; however, it was not inhibited at all by the addition of an isotype-matched control antibody.

To see whether the observed killing activity is mediated by the cytotoxic T-cells, effects of antibodies on the killing activities were investigated, in which antibodies recognizing T-cell surface antigens related to the function of CTL were used. CTL activities were clearly blocked by the addition of antibodies that recognize HLA Class I and CD8 but are affected little by the addition of antibodies to HLA Class II or CD4, as TTK-567 CTL clone shown in FIG. 10, URLC10-177 CTL clone in FIG. 11 and KOC1-508 CTL clone in FIG. 12. These results show that the cytotoxic activities of CTL clones against the lung carcinoma cells are the HLA class I restricted and CD8 mediated cytotoxic activity.

Homology Analysis of the Antigen Peptides

The CTL clones established against TTK-567, URLC10-177 or KOC1-508 showed potent cytotoxic activity. Thus, it is possible that the sequence of TTK-567, URLC10-177 or KOC1-508 is homologous to the peptides derived from other molecules, which are known to sensitize human immune system. To exclude this possibility, homology analysis was performed with the peptide sequences as queries using the BLAST algorithm (http://www.nbi.nlm.nih.gov/blast/blast.cgi) (Altschul S F, et al., (1997) Nucleic Acids Res.; 25(17):3389-402; Altschul F, et al., (1990) J Mol. Biol.; 215 (3):403-10) and revealed no sequence with significant homology. These results indicate that the sequences of TTK-567, URLC10-177 and KOC1-508 are unique and there is little possibility that the peptides would raise unintended immunologic responses to any unrelated molecule.

Discussion

Identification of new TAAs, particularly those that induce potent and specific anti-tumor immune responses, warrants further development of the clinical application of peptide vaccination strategies in various types of cancer (Boon T. et al., (1996) J Exp Med 183: 725-9; van der Bruggen P et al., (1991) Science 254: 1643-7; Brichard V et al., (1993) J Exp Med 178: 489-95; Kawakami Y et al., (1994) J Exp Med 180: 347-52; Shichijo S et al., (1998) J Exp Med 187:277-88; Chen Y T. et al., (1997) Proc. Natl. Acd. Sci. USA, 94: 1914-8; Harris C C., (1996) J Natl Cancer Inst 88:1442-5; Butterfield L H et al., (1999) Cancer Res 59:3134-42; Vissers J L et al., (1999) Cancer Res 59: 5554-9; van der Burg H et al., (1996) J. Immunol 156:3308-14; Tanaka F et al., (1997) Cancer Res 57:4465-8; Fujie T et al., (1999) Int J Cancer 80:169-72; Kikuchi M et al, (1999) Int J Cancer 81: 459-66; Oiso M et al., (1999) Int J Cancer 81:387-94).

cDNA microarray technologies can disclose comprehensive profiles of gene expression of malignant cells (Okabe H. et al, (2001) Cancer Res., 61, 2129-37; Lin Y-M. et al., (2002) Oncogene, 21; 4120-8; Hasegawa S. et al., (2002) Cancer Res 62:7012-7) and, find utility in the identification of potential TAAs. Among the transcripts that are up-regulated in lung cancers, three novel human genes, termed TTK, URLC10 and KOC1, respectively, were identified using these technologies.

As demonstrated above, TTK, URLC10 and KOC1 are over-expressed in lung cancer and show minimal expression in normal tissues. In addition, these genes have been shown to have a significant function related to cell proliferation (See WO2004/031413). Thus, peptides derived from TTK, URLC10 and KOC1 can serve as TAA epitopes, which, in turn, can be used to induce significant and specific immune responses against cancer cells.

Thus, as TTK, URLC10 and KOC1 are novel TAAs, cancer vaccines using these epitope peptides may be useful as immunotherapeutics against lung carcinoma or other cancer expressing these molecules.

INDUSTRIAL APPLICABILITY

The present invention identifies new TAAs, particularly those which induce potent and specific anti-tumor immune responses. Such TAAs warrants further development of the clinical application of peptide vaccination strategy in lung cancer.

All patents, patent applications, and publications cited herein are incorporated by reference.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

The invention claimed is:

1. An isolated peptide of the following (a) or (b):
   (a) a peptide of less than 15 amino acids selected from the group consisting of peptides comprising the amino acid sequences of SEQ ID NO: 8, 67, and 89, wherein the peptide has cytotoxic T cell inducibility, or
   (b) a peptide having cytotoxic T cell inducibility, wherein said peptide comprises an amino acid sequence selected from the group consisting of SEQ ID NO: 8, 67, and 89, wherein 1 or 2 amino acids are substituted, wherein the substitutions are selected from the group consisting of the second amino acid from the N-terminus is substituted with phenylalanine, tyrosine, methionine, or tryptophan, and the C-terminal amino acid is substituted with phenylalanine, leucine, isoleucine, tryptophan, or methionine.

2. A composition comprising one or more peptides of claim 1.

* * * * *

SEQUENCE LISTING

<160> NUMBER OF SEQ ID NOS: 126

<210> SEQ ID NO 1
<211> LENGTH: 2984
<212> TYPE: DNA
<213> ORGANISM: Homo sapiens

<400> SEQUENCE: 1

```
ggaaattcaa acgtgtttgc ggaaaggagt ttgggttcca tcttttcatt tccccagcgc      60
agctttctgt agaaatggaa tccgaggatt taagtggcag agaattgaca attgattcca     120
taatgaacaa agtgagagac attaaaaata agtttaaaaa tgaagacctt actgatgaac     180
```

-continued

```
taagcttgaa taaaatttct gctgatacta cagataactc gggaactgtt aaccaaatta      240
tgatgatggc aaacaaccca gaggactggt tgagtttgtt gctcaaacta gagaaaaaca      300
gtgttccgct aagtgatgct cttttaaata aattgattgg tcgttacagt caagcaattg      360
aagcgcttcc cccagataaa tatggccaaa atgagagttt gctagaatt caagtgagat       420 ttgctgaatt aaaagctatt caagagccag atgatgcacg tgactacttt caaatggcca      480
gagcaaactg caagaaattt gcttttgttc atatatcttt tgcacaattt gaactgtcac      540
aaggtaatgt caaaaaaagt aaacaacttc ttcaaaaagc tgtagaacgt ggagcagtac      600
cactagaaat gctggaaatt gccctgcgga atttaaacct ccaaaaaaag cagctgcttt      660
cagaggagga aaagaagaat ttatcagcat ctacggtatt aactgcccaa gaatcatttt      720
ccggttcact tgggcattta cagaatagga acaacagttg tgattccaga ggacagacta      780
ctaaagccag gtttttatat ggagagaaca tgccaccaca agatgcagaa ataggttacc      840
ggaattcatt gagacaaact aacaaaacta acagtcatg cccatttgga agagtcccag       900
ttaaccttct aaatagccca gattgtgatg tgaagacaga tgattcagtt gtaccttgtt      960
ttatgaaaag acaaacctct agatcagaat gccgagattt ggttgtgcct ggatctaaac     1020
caagtggaaa tgattcctgt gaattaagaa atttaaagtc tgttcaaaat agtcatttca     1080
aggaacctct ggtgtcagat gaaaagagtt ctgaacttat tattactgat tcaataaccc     1140
tgaagaataa aacggaatca agtcttctag ctaaattaga agaaactaaa gagtatcaag     1200
aaccagaggt tccagagagt aaccagaaac agtggcaatc taagagaaag tcagagtgta     1260
ttaaccagaa tcctgctgca tcttcaaatc actggcagat tccggagtta gcccgaaaag     1320
ttaatacaga gcagaaacat accacttttg agcaacctgt cttttcagtt tcaaaacagt     1380
caccaccaat atcaacatct aaatggtttg acccaaaatc tatttgtaag acaccaagca     1440
gcaatacctt ggatgattac atgagctgtt ttagaactcc agttgtaaag aatgactttc     1500
cacctgcttg tcagttgtca acaccttatg gccaacctgc ctgtttccag cagcaacagc     1560
atcaaatact tgccactcca cttcaaaatt tacaggtttt agcatcttct tcagcaaatg     1620
aatgcatttc ggttaaagga agaatttatt ccatttaaa gcagatagga agtggaggtt      1680
caagcaaggt atttcaggtg ttaaatgaaa agaaacagat atatgctata aaatatgtga     1740
acttagaaga agcagataac caaactcttg atagttaccg gaacgaaata gcttatttga     1800
ataaactaca caacacagt gataagatca tccgacttta tgattatgaa atcacggacc      1860
agtacatcta catggtaatg gagtgtggaa atattgatct taatagttgg cttaaaaaga     1920
aaaaatccat tgatccatgg gaacgcaaga gttactggaa aaatatgtta gaggcagttc     1980
acacaatcca tcaacatggc attgttcaca gtgatcttaa ccagctaac tttctgatag      2040 ttgatggaat gctaaagcta attgattttg ggattgcaaa ccaaatgcaa ccagatacaa     2100
caagtgttgt taaagattct caggttggca cagttaatta tatgccacca gaagcaatca     2160
aagatatgtc ttcctccaga gagaatggga atctaagtc aaagataagc cccaaaagtg      2220
atgtttggtc cttaggatgt attttgtact atatgactta cgggaaaaca ccatttcagc     2280
agataattaa tcagatttct aaattacatg ccataattga tcctaatcat gaaattgaat     2340
ttcccgatat tccagagaaa gatcttcaag atgtgttaaa gtgttgttta aaagggacc      2400 caaaacagag gatatccatt cctgagctcc tggctcatcc ctatgttcaa attcaaactc     2460
atccagttaa ccaatggcc aagggaacca ctgaagaaat gaatatgtt ctgggccaac       2520 ttgttggtct gaattctcct aactccattt tgaaagctgc taaaacttta tatgaacact     2580
```

```
atagtggtgg tgaaagtcat aattcttcat cctccaagac ttttgaaaaa aaaaggggaa    2640
aaaaatgatt tgcagttatt cgtaatgtca ataccacct  ataaaatata ttggactgtt    2700
atactcttga atccctgtgg aaatctacat ttgaagacaa catcactctg aagtgttatc    2760
agcaaaaaaa attcagtaga ttatctttaa aagaaaactg taaaaatagc aaccacttat    2820
ggtactgtat atattgtaga cttgttttct ctgttttatg ctcttgtgta atctacttga    2880
catcatttta ctcttggaat agtgggtgga tagcaagtat attctaaaaa actttgtaaa    2940
taaagttttg tggctaaaat gacactaaaa aaaaaaaaaa aaaa                    2984
```

<210> SEQ ID NO 2
<211> LENGTH: 857
<212> TYPE: PRT
<213> ORGANISM: Homo sapiens

<400> SEQUENCE: 2

```
Met Glu Ser Glu Asp Leu Ser Gly Arg Glu Leu Thr Ile Asp Ser Ile
  1               5                  10                  15

Met Asn Lys Val Arg Asp Ile Lys Asn Lys Phe Lys Asn Glu Asp Leu
                 20                  25                  30

Thr Asp Glu Leu Ser Leu Asn Lys Ile Ser Ala Asp Thr Thr Asp Asn
             35                  40                  45

Ser Gly Thr Val Asn Gln Ile Met Met Met Ala Asn Asn Pro Glu Asp
         50                  55                  60

Trp Leu Ser Leu Leu Lys Leu Glu Lys Asn Ser Val Pro Leu Ser
 65                  70                  75                  80

Asp Ala Leu Leu Asn Lys Leu Ile Gly Arg Tyr Ser Gln Ala Ile Glu
                 85                  90                  95

Ala Leu Pro Pro Asp Lys Tyr Gly Gln Asn Glu Ser Phe Ala Arg Ile
                100                 105                 110

Gln Val Arg Phe Ala Glu Leu Lys Ala Ile Gln Glu Pro Asp Asp Ala
            115                 120                 125

Arg Asp Tyr Phe Gln Met Ala Arg Ala Asn Cys Lys Lys Phe Ala Phe
        130                 135                 140

Val His Ile Ser Phe Ala Gln Phe Glu Leu Ser Gln Gly Asn Val Lys
145                 150                 155                 160

Lys Ser Lys Gln Leu Leu Gln Lys Ala Val Glu Arg Gly Ala Val Pro
                165                 170                 175

Leu Glu Met Leu Glu Ile Ala Leu Arg Asn Leu Asn Leu Gln Lys Lys
            180                 185                 190

Gln Leu Leu Ser Glu Glu Glu Lys Lys Asn Leu Ser Ala Ser Thr Val
        195                 200                 205

Leu Thr Ala Gln Glu Ser Phe Ser Gly Ser Leu Gly His Leu Gln Asn
    210                 215                 220

Arg Asn Asn Ser Cys Asp Ser Arg Gly Gln Thr Thr Lys Ala Arg Phe
225                 230                 235                 240

Leu Tyr Gly Glu Asn Met Pro Pro Gln Asp Ala Glu Ile Gly Tyr Arg
                245                 250                 255

Asn Ser Leu Arg Gln Thr Asn Lys Thr Lys Gln Ser Cys Pro Phe Gly
            260                 265                 270

Arg Val Pro Val Asn Leu Leu Asn Ser Pro Asp Cys Asp Val Lys Thr
        275                 280                 285

Asp Asp Ser Val Val Pro Cys Phe Met Lys Arg Gln Thr Ser Arg Ser
    290                 295                 300
```

```
Glu Cys Arg Asp Leu Val Val Pro Gly Ser Lys Pro Ser Gly Asn Asp
305                 310                 315                 320

Ser Cys Glu Leu Arg Asn Leu Lys Ser Val Gln Asn Ser His Phe Lys
            325                 330                 335

Glu Pro Leu Val Ser Asp Glu Lys Ser Ser Glu Leu Ile Ile Thr Asp
                340                 345                 350

Ser Ile Thr Leu Lys Asn Lys Thr Glu Ser Ser Leu Leu Ala Lys Leu
            355                 360                 365

Glu Glu Thr Lys Glu Tyr Gln Glu Pro Glu Val Pro Glu Ser Asn Gln
370                 375                 380

Lys Gln Trp Gln Ser Lys Arg Lys Ser Glu Cys Ile Asn Gln Asn Pro
385                 390                 395                 400

Ala Ala Ser Ser Asn His Trp Gln Ile Pro Glu Leu Ala Arg Lys Val
                405                 410                 415

Asn Thr Glu Gln Lys His Thr Thr Phe Glu Gln Pro Val Phe Ser Val
            420                 425                 430

Ser Lys Gln Ser Pro Pro Ile Ser Thr Ser Lys Trp Phe Asp Pro Lys
            435                 440                 445

Ser Ile Cys Lys Thr Pro Ser Ser Asn Thr Leu Asp Asp Tyr Met Ser
            450                 455                 460

Cys Phe Arg Thr Pro Val Val Lys Asn Asp Phe Pro Pro Ala Cys Gln
465                 470                 475                 480

Leu Ser Thr Pro Tyr Gly Gln Pro Ala Cys Phe Gln Gln Gln His
                485                 490                 495

Gln Ile Leu Ala Thr Pro Leu Gln Asn Leu Gln Val Leu Ala Ser Ser
            500                 505                 510

Ser Ala Asn Glu Cys Ile Ser Val Lys Gly Arg Ile Tyr Ser Ile Leu
            515                 520                 525

Lys Gln Ile Gly Ser Gly Gly Ser Ser Lys Val Phe Gln Val Leu Asn
            530                 535                 540

Glu Lys Lys Gln Ile Tyr Ala Ile Lys Tyr Val Asn Leu Glu Glu Ala
545                 550                 555                 560

Asp Asn Gln Thr Leu Asp Ser Tyr Arg Asn Glu Ile Ala Tyr Leu Asn
            565                 570                 575

Lys Leu Gln Gln His Ser Asp Lys Ile Ile Arg Leu Tyr Asp Tyr Glu
            580                 585                 590

Ile Thr Asp Gln Tyr Ile Tyr Met Val Met Glu Cys Gly Asn Ile Asp
            595                 600                 605

Leu Asn Ser Trp Leu Lys Lys Lys Ser Ile Asp Pro Trp Glu Arg
610                 615                 620

Lys Ser Tyr Trp Lys Asn Met Leu Glu Ala Val His Thr Ile His Gln
625                 630                 635                 640

His Gly Ile Val His Ser Asp Leu Lys Pro Ala Asn Phe Leu Ile Val
                645                 650                 655

Asp Gly Met Leu Lys Leu Ile Asp Phe Gly Ile Ala Asn Gln Met Gln
            660                 665                 670

Pro Asp Thr Thr Ser Val Val Lys Asp Ser Gln Val Gly Thr Val Asn
            675                 680                 685

Tyr Met Pro Pro Glu Ala Ile Lys Asp Met Ser Ser Arg Glu Asn
            690                 695                 700

Gly Lys Ser Lys Ser Lys Ile Ser Pro Lys Ser Asp Val Trp Ser Leu
705                 710                 715                 720
```

```
Gly Cys Ile Leu Tyr Tyr Met Thr Tyr Gly Lys Thr Pro Phe Gln Gln
            725                 730                 735
Ile Ile Asn Gln Ile Ser Lys Leu His Ala Ile Ile Asp Pro Asn His
        740                 745                 750
Glu Ile Glu Phe Pro Asp Ile Pro Glu Lys Asp Leu Gln Asp Val Leu
            755                 760                 765
Lys Cys Cys Leu Lys Arg Asp Pro Lys Gln Arg Ile Ser Ile Pro Glu
    770                 775                 780
Leu Leu Ala His Pro Tyr Val Gln Ile Gln Thr His Pro Val Asn Gln
785                 790                 795                 800
Met Ala Lys Gly Thr Thr Glu Glu Met Lys Tyr Val Leu Gly Gln Leu
                805                 810                 815
Val Gly Leu Asn Ser Pro Asn Ser Ile Leu Lys Ala Ala Lys Thr Leu
            820                 825                 830
Tyr Glu His Tyr Ser Gly Gly Glu Ser His Asn Ser Ser Ser Ser Lys
            835                 840                 845
Thr Phe Glu Lys Lys Arg Gly Lys Lys
850                 855
```

<210> SEQ ID NO 3
<211> LENGTH: 1214
<212> TYPE: DNA
<213> ORGANISM: Homo sapiens

<400> SEQUENCE: 3

```
aacggcccag gcaggggcct tactagtaag cacgttttgg gaagtcctca gggcacgcag      60
gcaccgtgac ctcacacact agtgcgctgg agtgtgtcat tagcatctgg aatctctccc     120
cagggatgtg gtttttgttt gttttttttt tttttttttgg tattataatg agctaaaagc     180
tattcagggg cgagttatca gaggtgagcc cgtgctcttc agcggagaag atcccctacc     240
tggccgccgg ccactttctg tgggccgtgg ggtcctcaag gagacggccc ttgggctcag     300
gggctgcgtt tccacacgcg cctttcccag ggctcccgcg cccgttcctg cctggccgcc     360
ggccgctcca acagcagcac aaggcgggac tcagaaccgg cgttcagggc cgccagcggc     420
cgcgaggccc tgagatgagg ctccaaagac cccgacaggc cccggcgggt gggaggcgcg     480
cgccccgggg cgggcgggc tcccctacc ggccagaccc ggggagaggc gcgcggaggc     540
tgcgaaggtt ccagaagggc ggggaggggg cgccgcgcgc tgaccctccc tgggcaccgc     600
tggggacgat ggcgctgctc gccttgctgc tggtcgtggc cctaccgcgg gtgtggacag     660
acgccaacct gactgcgaga caacgagatc cagaggactc ccagcgaacg gacgagggtg     720
acaatagagt gtggtgtcat gtttgtgaga gagaaacac tttcgagtgc cagaacccaa     780
ggaggtgcaa atggacagag ccatactgcg ttatagcggc cgtgaaaata tttccacgtt     840
ttttcatggt tgcgaagcag tgctccgctg gttgtgcagc gatggagaga cccaagccag     900
aggagaagcg gtttctcctg gaagagccca tgcccttctt ttacctcaag tgttgtaaaa     960
ttcgctactg caatttagag gggccaccta tcaactcatc agtgttcaaa gaatatgctg    1020
ggagcatggg tgagagctgt ggtgggctgt ggctggccat cctcctgctg ctggcctcca    1080
ttgcagccgg cctcagcctg tcttgagcca cgggactgcc acagactgag ccttccggag    1140
catggactcg ctccagaccg ttgtcacctg ttgcattaaa cttgtttcct gttgaaaaaa    1200
aaaaaaaaaa aaaa                                                      1214
```

<210> SEQ ID NO 4
<211> LENGTH: 223
<212> TYPE: PRT
<213> ORGANISM: Homo sapiens

<400> SEQUENCE: 4

```
Met Arg Leu Gln Arg Pro Arg Gln Ala Pro Ala Gly Gly Arg Ala
1               5                   10                  15

Pro Arg Gly Gly Arg Gly Ser Pro Tyr Arg Pro Asp Pro Gly Arg Gly
                20                  25                  30

Ala Arg Arg Leu Arg Arg Phe Gln Lys Gly Gly Glu Gly Ala Pro Arg
            35                  40                  45

Ala Asp Pro Pro Trp Ala Pro Leu Gly Thr Met Ala Leu Leu Ala Leu
        50                  55                  60

Leu Leu Val Val Ala Leu Pro Arg Val Trp Thr Asp Ala Asn Leu Thr
65                  70                  75                  80

Ala Arg Gln Arg Asp Pro Glu Asp Ser Gln Arg Thr Asp Glu Gly Asp
                85                  90                  95

Asn Arg Val Trp Cys His Val Cys Glu Arg Glu Asn Thr Phe Glu Cys
                100                 105                 110

Gln Asn Pro Arg Arg Cys Lys Trp Thr Glu Pro Tyr Cys Val Ile Ala
            115                 120                 125

Ala Val Lys Ile Phe Pro Arg Phe Phe Met Val Ala Lys Gln Cys Ser
        130                 135                 140

Ala Gly Cys Ala Ala Met Glu Arg Pro Lys Pro Glu Glu Lys Arg Phe
145                 150                 155                 160

Leu Leu Glu Glu Pro Met Pro Phe Phe Tyr Leu Lys Cys Cys Lys Ile
                165                 170                 175

Arg Tyr Cys Asn Leu Glu Gly Pro Pro Ile Asn Ser Ser Val Phe Lys
            180                 185                 190

Glu Tyr Ala Gly Ser Met Gly Glu Ser Cys Gly Gly Leu Trp Leu Ala
        195                 200                 205

Ile Leu Leu Leu Leu Ala Ser Ile Ala Ala Gly Leu Ser Leu Ser
    210                 215                 220
```

<210> SEQ ID NO 5
<211> LENGTH: 4168
<212> TYPE: DNA
<213> ORGANISM: Homo sapiens

<400> SEQUENCE: 5

```
aagacttagg aagactggtg gatgcgtttg ggttgtagct aggcttttc ttttctttct    60 cttttaaaac acatctagac aaggaaaaaa caagcctcgg atctgatttt tcactcctcg   120
ttcttgtgct tggttcttac tgtgtttgtg tattttaaag gcgagaagac gaggggaaca   180
aaaccagctg gatccatcca tcaccgtggg tggttttaat ttttcgtttt ttctcgttat   240 tttttttaa acaaccactc ttcacaatga acaaactgta tatcggaaac ctcagcgaga   300
acgccgcccc ctcggaccta gaaagtatct tcaaggacgc caagatcccg gtgtcgggac   360
ccttcctggt gaagactggc tacgcgttcg tggactgccc ggacgagagc tgggcctca   420 aggccatcga ggcgctttca ggtaaaatag aactgcacgg gaaacccata gaagttgagc   480
actcggtccc aaaaaggcaa aggattcgga aacttcagat acgaaatatc ccgcctcatt   540
tacagtggga ggtgctggat agtttactag tccagtatgg agtggtggag agctgtgagc   600
```

```
aagtgaacac tgactcggaa actgcagttg taaatgtaac ctattccagt aaggaccaag    660
ctagacaagc actagacaaa ctgaatggat ttcagttaga gaatttcacc ttgaaagtag    720
cctatatccc tgatgaaatg gccgcccagc aaaacccctt gcagcagccc cgaggtcgcc    780
gggggcttgg gcagaggggc tcctcaaggc aggggtctcc aggatccgta tccaagcaga    840
aaccatgtga tttgcctctg cgcctgctgg ttcccaccca atttgttgga gccatcatag    900
gaaaagaagg tgccaccatt cggaacatca ccaaacagac ccagtctaaa atcgatgtcc    960
accgtaaaga aaatgcgggg gctgctgaga agtcgattac tatcctctct actcctgaag   1020
gcacctctgc ggcttgtaag tctattctgg agattatgca taaggaagct caagatataa   1080
aattcacaga agagatcccc ttgaagattt tagctcataa taactttgtt ggacgtctta   1140
ttggtaaaga aggaagaaat cttaaaaaaa ttgagcaaga cacagacact aaaatcacga   1200
tatctccatt gcaggaattg acgctgtata atccagaacg cactattaca gttaaaggca   1260
atgttgagac atgtgccaaa gctgaggagg agatcatgaa gaaaatcagg gagtcttatg   1320
aaaatgatat tgcttctatg aatcttcaag cacatttaat tcctggatta aatctgaacg   1380
ccttgggtct gttcccaccc acttcaggga tgccacctcc cacctcaggg ccccttcag    1440 ccatgactcc tccctacccg cagtttgagc aatcagaaac ggagactgtt catctgttta   1500
tcccagctct atcagtcggt gccatcatcg gcaagcaggg ccagcacatc aagcagcttt   1560
ctcgctttgc tggagcttca attaagattg ctccagcgga agcaccagat gctaaagtga   1620
ggatggtgat tatcactgga ccaccagagg ctcagttcaa ggctcaggga agaatttatg   1680
gaaaaattaa agaagaaaac tttgttagtc ctaaagaaga ggtgaaactt gaagctcata   1740
tcagagtgcc atccttttgct gctggcagag ttattggaaa aggaggcaaa acggtgaatg   1800
aacttcagaa tttgtcaagt gcagaagttg ttgtccctcg tgaccagaca cctgatgaga   1860
atgaccaagt ggttgtcaaa ataactggtc acttctatgc ttgccaggtt gcccagagaa   1920
aaattcagga aattctgact caggtaaagc agcaccaaca acagaaggct ctgcaaagtg   1980
gaccacctca gtcaagacgg aagtaaaggc tcaggaaaca gcccaccaca gaggcagatg   2040
ccaaaccaaa gacagattgc ttaaccaaca gatgggcgct gaccccctat ccagaatcac   2100
atgcacaagt ttttacctag ccagttgttt ctgaggacca ggcaactttt gaactcctgt   2160
ctctgtgaga atgtatactt tatgctctct gaaatgtatg acacccagct ttaaaacaaa   2220
caaacaaaca aacaaaaaaa gggtggggga gggaggaa gagaagagct ctgcacttcc   2280
ctttgttgta gtctcacagt ataacagata ttctaattct tcttaatatt cccccataat   2340
gccagaaatt ggcttaatga tgctttcact aaattcatca aatagattgc tcctaaatcc   2400
aattgttaaa attggatcag ataattatc acaggaactt aaatgttaag ccattagcat   2460
agaaaaactg ttctcagttt tatttttacc taacactaac atgagtaacc taagggaagt   2520
gctgaatggt gttggcaggg gtattaaacg tgcattttta ctcaactacc tcaggtattc   2580
agtaatacaa tgaaaagcaa aattgttcct ttttttgaa aattttatat actttataat   2640
gatagaagtc caaccgtttt ttaaaaaata aatttaaaat ttaacagcaa tcagctaaca   2700
ggcaaattaa gatttttact tctggctggt gacagtaaag ctggaaaatt aatttcaggg   2760
ttttttgagg cttttgacac agttattagt taaatcaaat gttcaaaaat acggagcagt   2820
gcctagtatc tggagagcag cactaccatt tattctttca tttatagttg ggaaagtttt   2880
tgacggtact aacaaagtgg tcgcaggaga ttttggaacg gctggtttaa atggcttcag   2940
gagacttcag tttttttgttt agctacatga ttgaatgcat aataaatgct ttgtgcttct   3000
```

-continued

```
gactatcaat acctaaagaa agtgcatcag tgaagagatg caagactttc aactgactgg      3060
caaaaagcaa gctttagctt gtcttatagg atgcttagtt tgccactaca cttcagacca      3120
atgggacagt catagatggt gtgacagtgt ttaaacgcaa caaaaggcta catttccatg      3180
gggccagcac tgtcatgagc ctcactaagc tattttgaag attttttaagc actgataaat      3240 taaaaaaaaa aaattagact ccaccttaag tagtaaagta taacaggatt tctgtatact      3300
gtgcaatcag ttctttgaaa aaaaagtcaa aagatagaga atacaagaaa agttttgggg      3360
atataatttg aatgactgtg aaaacatatg acctttgata acgaactcat ttgctcactc      3420
cttgacagca aagcccagta cgtacaattg tgttgggtgt gggtggtctc caaggccacg      3480
ctgctctctg aattgatttt ttgagttttg tttgtaagat gatcacagtc atgttacact      3540
gatctaaagg acatatatat aaccctttaa aaaaaaaatc actgcctcat tcttatttca      3600
agatgaattt ctatacagac tagatgtttt tctgaagatc aattagacat tttgaaaatg      3660
atttaaagtg ttttccttaa tgttctctga aaacaagttt cttttgtagt tttaaccaaa      3720
aaagtgccct ttttgtcact ggattctcct agcattcatg atttttttttt catacaatga      3780 attaaaattg ctaaaatcat ggactggctt tctggttgga tttcaggtaa gatgtgttta      3840
aggccagagc ttttctcagt atttgatttt ttttccccaat atttgatttt ttaaaaatat      3900
acacataggt gctgcattta tatctgctgg tttaaattct gtcatatttc acttctagcc      3960
ttttagtatg gcaaatcata ttttactttt acttaagcat ttgtaatttg gagtatctgg      4020
tactagctaa gaaataattc tataattgag ttttgtactc accatatatg gatcattcct      4080
catgtataat gtgccccaaa tgcagcttca ttttccagat accttgacgc agaataaatt      4140
ttttcatcat ttaggtgcaa aaaaaaaa                                         4168
```

<210> SEQ ID NO 6
<211> LENGTH: 579
<212> TYPE: PRT
<213> ORGANISM: Homo sapiens

<400> SEQUENCE: 6

```
Met Asn Lys Leu Tyr Ile Gly Asn Leu Ser Glu Asn Ala Ala Pro Ser
1               5                   10                  15

Asp Leu Glu Ser Ile Phe Lys Asp Ala Lys Ile Pro Val Ser Gly Pro
            20                  25                  30

Phe Leu Val Lys Thr Gly Tyr Ala Phe Val Asp Cys Pro Asp Glu Ser
        35                  40                  45

Trp Ala Leu Lys Ala Ile Glu Ala Leu Ser Gly Lys Ile Glu Leu His
    50                  55                  60

Gly Lys Pro Ile Glu Val Glu His Ser Val Pro Lys Arg Gln Arg Ile
65                  70                  75                  80

Arg Lys Leu Gln Ile Arg Asn Ile Pro Pro His Leu Gln Trp Glu Val
                85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140

Glu Asn Phe Thr Leu Lys Val Ala Tyr Ile Pro Asp Glu Met Ala Ala
145                 150                 155                 160
```

```
Gln Gln Asn Pro Leu Gln Gln Pro Arg Gly Arg Arg Gly Leu Gly Gln
                165                 170                 175
Arg Gly Ser Ser Arg Gln Gly Ser Pro Gly Ser Val Ser Lys Gln Lys
            180                 185                 190
Pro Cys Asp Leu Pro Leu Arg Leu Leu Val Pro Thr Gln Phe Val Gly
        195                 200                 205
Ala Ile Ile Gly Lys Glu Gly Ala Thr Ile Arg Asn Ile Thr Lys Gln
    210                 215                 220
Thr Gln Ser Lys Ile Asp Val His Arg Lys Glu Asn Ala Gly Ala Ala
225                 230                 235                 240
Glu Lys Ser Ile Thr Ile Leu Ser Thr Pro Glu Gly Thr Ser Ala Ala
                245                 250                 255
Cys Lys Ser Ile Leu Glu Ile Met His Lys Glu Ala Gln Asp Ile Lys
            260                 265                 270
Phe Thr Glu Glu Ile Pro Leu Lys Ile Leu Ala His Asn Asn Phe Val
        275                 280                 285
Gly Arg Leu Ile Gly Lys Glu Gly Arg Asn Leu Lys Lys Ile Glu Gln
    290                 295                 300
Asp Thr Asp Thr Lys Ile Thr Ile Ser Pro Leu Gln Glu Leu Thr Leu
305                 310                 315                 320
Tyr Asn Pro Glu Arg Thr Ile Thr Val Lys Gly Asn Val Glu Thr Cys
                325                 330                 335
Ala Lys Ala Glu Glu Glu Ile Met Lys Lys Ile Arg Glu Ser Tyr Glu
            340                 345                 350
Asn Asp Ile Ala Ser Met Asn Leu Gln Ala His Leu Ile Pro Gly Leu
        355                 360                 365
Asn Leu Asn Ala Leu Gly Leu Phe Pro Pro Thr Ser Gly Met Pro Pro
    370                 375                 380
Pro Thr Ser Gly Pro Pro Ser Ala Met Thr Pro Pro Tyr Pro Gln Phe
385                 390                 395                 400
Glu Gln Ser Glu Thr Glu Thr Val His Leu Phe Ile Pro Ala Leu Ser
                405                 410                 415
Val Gly Ala Ile Ile Gly Lys Gln Gly Gln His Ile Lys Gln Leu Ser
            420                 425                 430
Arg Phe Ala Gly Ala Ser Ile Lys Ile Ala Pro Ala Glu Ala Pro Asp
        435                 440                 445
Ala Lys Val Arg Met Val Ile Ile Thr Gly Pro Pro Glu Ala Gln Phe
    450                 455                 460
Lys Ala Gln Gly Arg Ile Tyr Gly Lys Ile Lys Glu Glu Asn Phe Val
465                 470                 475                 480
Ser Pro Lys Glu Glu Val Lys Leu Glu Ala His Ile Arg Val Pro Ser
                485                 490                 495
Phe Ala Ala Gly Arg Val Ile Gly Lys Gly Gly Lys Thr Val Asn Glu
            500                 505                 510
Leu Gln Asn Leu Ser Ser Ala Glu Val Val Pro Arg Asp Gln Thr
        515                 520                 525
Pro Asp Glu Asn Asp Gln Val Val Lys Ile Thr Gly His Phe Tyr
    530                 535                 540
Ala Cys Gln Val Ala Gln Arg Lys Ile Gln Glu Ile Leu Thr Gln Val
545                 550                 555                 560
Lys Gln His Gln Gln Gln Lys Ala Leu Gln Ser Gly Pro Pro Gln Ser
                565                 570                 575
Arg Arg Lys
```

<210> SEQ ID NO 7
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 7

Arg Tyr Ser Gln Ala Ile Glu Ala Leu
1               5

<210> SEQ ID NO 8
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 8

Ser Tyr Arg Asn Glu Ile Ala Tyr Leu
1               5

<210> SEQ ID NO 9
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 9

Ile Tyr Ala Ile Lys Tyr Val Asn Leu
1               5

<210> SEQ ID NO 10
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 10

Asp Tyr Glu Ile Thr Asp Gln Tyr Ile
1               5

<210> SEQ ID NO 11
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 11

Asn Phe Leu Ile Val Asp Gly Met Leu
1               5

<210> SEQ ID NO 12
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 12

Lys Phe Ala Phe Val His Ile Ser Phe
1               5

```
<210> SEQ ID NO 13
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 13

Ser Phe Ser Gly Ser Leu Gly His Leu
1               5

<210> SEQ ID NO 14
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 14

Lys Asn Glu Asp Leu Thr Asp Glu Leu
1               5

<210> SEQ ID NO 15
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 15

Arg Ile Gln Val Arg Phe Ala Glu Leu
1               5

<210> SEQ ID NO 16
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 16

Ser Phe Ala Arg Ile Gln Val Arg Phe
1               5

<210> SEQ ID NO 17
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 17

Lys Leu Glu Lys Asn Ser Val Pro Leu
1               5

<210> SEQ ID NO 18
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 18

Lys Asn Leu Ser Ala Ser Thr Val Leu
1               5
```

```
<210> SEQ ID NO 19
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 19

Arg Thr Pro Val Val Lys Asn Asp Phe
1               5

<210> SEQ ID NO 20
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 20

Lys Tyr Gly Gln Asn Glu Ser Phe Ala
1               5

<210> SEQ ID NO 21
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 21

Lys Val Arg Asp Ile Lys Asn Lys Phe
1               5

<210> SEQ ID NO 22
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 22

Lys Gln Arg Ile Ser Ile Pro Glu Leu
1               5

<210> SEQ ID NO 23
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 23

Asn Ser Val Pro Leu Ser Asp Ala Leu
1               5

<210> SEQ ID NO 24
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 24

Gly Asn Ile Asp Leu Asn Ser Trp Leu
1               5

<210> SEQ ID NO 25
```

```
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 25

Gln Tyr Ile Tyr Met Val Met Glu Cys
1               5

<210> SEQ ID NO 26
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 26

Gly Ser Ser Lys Val Phe Gln Val Leu
1               5

<210> SEQ ID NO 27
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 27

Lys Tyr Val Leu Gly Gln Leu Val Gly Leu
1               5                   10

<210> SEQ ID NO 28
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 28

Tyr Tyr Met Thr Tyr Gly Lys Thr Pro Phe
1               5                   10

<210> SEQ ID NO 29
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 29

Ile Tyr Met Val Met Glu Cys Gly Asn Ile
1               5                   10

<210> SEQ ID NO 30
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 30

Thr Tyr Gly Lys Thr Pro Phe Gln Gln Ile
1               5                   10

<210> SEQ ID NO 31
<211> LENGTH: 10
```

```
<212> TYPE: PRT
<213> ORGANISM: Artificial
<220> FEATURE:
<223> OTHER INFORMATION: An artificially synthesized peptide sequense.

<400> SEQUENCE: 31

Glu Phe Pro Asp Ile Pro Glu Lys Asp Leu
1               5                   10

<210> SEQ ID NO 32
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 32

Cys Phe Gln Gln Gln Gln His Gln Ile Leu
1               5                   10

<210> SEQ ID NO 33
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 33

Ala Phe Val His Ile Ser Phe Ala Gln Phe
1               5                   10

<210> SEQ ID NO 34
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 34

Arg Asn Glu Ile Ala Tyr Leu Asn Lys Leu
1               5                   10

<210> SEQ ID NO 35
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 35

Lys Thr Glu Ser Ser Leu Leu Ala Lys Leu
1               5                   10

<210> SEQ ID NO 36
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 36

Lys Tyr Val Asn Leu Glu Glu Ala Asp Asn
1               5                   10

<210> SEQ ID NO 37
<211> LENGTH: 10
<212> TYPE: PRT
```

```
<213> ORGANISM: Artificial
<220> FEATURE:
<223> OTHER INFORMATION: An artificially synthesized peptide sequense.

<400> SEQUENCE: 37

Lys Ala Val Glu Arg Gly Ala Val Pro Leu
1               5                   10

<210> SEQ ID NO 38
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 38

Arg Gly Gln Thr Thr Lys Ala Arg Phe Leu
1               5                   10

<210> SEQ ID NO 39
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 39

Arg Asn Leu Asn Leu Gln Lys Lys Gln Leu
1               5                   10

<210> SEQ ID NO 40
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 40

Lys Gln Arg Ile Ser Ile Pro Glu Leu Leu
1               5                   10

<210> SEQ ID NO 41
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 41

Ala Tyr Leu Asn Lys Leu Gln Gln His Ser
1               5                   10

<210> SEQ ID NO 42
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 42

Glu Tyr Gln Glu Pro Glu Val Pro Glu Ser
1               5                   10

<210> SEQ ID NO 43
<211> LENGTH: 10
<212> TYPE: PRT
<213> ORGANISM: Artificial
```

```
<220> FEATURE:
<223> OTHER INFORMATION: An artificially synthesized peptide sequense.

<400> SEQUENCE: 43

Lys Asn Ser Val Pro Leu Ser Asp Ala Leu
1               5                   10

<210> SEQ ID NO 44
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 44

Lys Pro Ser Gly Asn Asp Ser Cys Glu Leu
1               5                   10

<210> SEQ ID NO 45
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 45

Asn Pro Glu Asp Trp Leu Ser Leu Leu Leu
1               5                   10

<210> SEQ ID NO 46
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 46

Asp Leu Gln Asp Val Leu Lys Cys Cys Leu
1               5                   10

<210> SEQ ID NO 47
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 47

Lys Pro Glu Glu Lys Arg Phe Leu Leu
1               5

<210> SEQ ID NO 48
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 48

Arg Ala Asp Pro Pro Trp Ala Pro Leu
1               5

<210> SEQ ID NO 49
<211> LENGTH: 9
<212> TYPE: PRT
<213> ORGANISM: Artificial
<220> FEATURE:
```

<223> OTHER INFORMATION: An artificially synthesized peptide sequense.

<400> SEQUENCE: 49

Leu Trp Leu Ala Ile Leu Leu Leu Leu
1               5

<210> SEQ ID NO 50
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 50

Gly Thr Met Ala Leu Leu Ala Leu Leu
1               5

<210> SEQ ID NO 51
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 51

Gly Gly Leu Trp Leu Ala Ile Leu Leu
1               5

<210> SEQ ID NO 52
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 52

Leu Ala Leu Leu Leu Val Val Ala Leu
1               5

<210> SEQ ID NO 53
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 53

Trp Ala Pro Leu Gly Thr Met Ala Leu
1               5

<210> SEQ ID NO 54
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 54

Ala Ser Ile Ala Ala Gly Leu Ser Leu
1               5

<210> SEQ ID NO 55
<211> LENGTH: 9
<212> TYPE: PRT
<213> ORGANISM: Artificial
<220> FEATURE:
<223> OTHER INFORMATION: An artificially synthesized peptide sequense.

-continued

<400> SEQUENCE: 55

Ala Pro Leu Gly Thr Met Ala Leu Leu
1               5

<210> SEQ ID NO 56
<211> LENGTH: 9
<212> TYPE: PRT
<213> ORGANISM: Artificial
<220> FEATURE:
<223> OTHER INFORMATION: An artificially synthesized peptide sequence.

<400> SEQUENCE: 56

Leu Leu Ala Ser Ile Ala Ala Gly Leu
1               5

<210> SEQ ID NO 57
<211> LENGTH: 9
<212> TYPE: PRT
<213> ORGANISM: Artificial
<220> FEATURE:
<223> OTHER INFORMATION: An artificially synthesized peptide sequence.

<400> SEQUENCE: 57

Glu Tyr Ala Gly Ser Met Gly Glu Ser
1               5

<210> SEQ ID NO 58
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 58

Phe Phe Tyr Leu Lys Cys Cys Lys Ile
1               5

<210> SEQ ID NO 59
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 59

Ala Ala Val Lys Ile Phe Pro Arg Phe
1               5

<210> SEQ ID NO 60
<211> LENGTH: 9
<212> TYPE: PRT
<213> ORGANISM: Artificial
<220> FEATURE:
<223> OTHER INFORMATION: An artificially synthesized peptide sequence.

<400> SEQUENCE: 60

Thr Met Ala Leu Leu Ala Leu Leu Leu
1               5

<210> SEQ ID NO 61
<211> LENGTH: 9
<212> TYPE: PRT
<213> ORGANISM: Artificial
<220> FEATURE:
<223> OTHER INFORMATION: An artificially synthesized peptide sequense.

```
<400> SEQUENCE: 61

Arg Pro Lys Pro Glu Glu Lys Arg Phe
1               5

<210> SEQ ID NO 62
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 62

Ser Met Gly Glu Ser Cys Gly Gly Leu
1               5

<210> SEQ ID NO 63
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 63

Cys Cys Lys Ile Arg Tyr Cys Asn Leu
1               5

<210> SEQ ID NO 64
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 64

Asp Pro Gly Arg Gly Ala Arg Arg Leu
1               5

<210> SEQ ID NO 65
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 65

Arg Gly Ala Arg Arg Leu Arg Arg Phe
1               5

<210> SEQ ID NO 66
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 66

Cys Gly Gly Leu Trp Leu Ala Ile Leu
1               5

<210> SEQ ID NO 67
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 67
```

Arg Tyr Cys Asn Leu Glu Gly Pro Pro Ile
1               5                   10

<210> SEQ ID NO 68
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 68

Arg Phe Leu Leu Glu Glu Pro Met Pro Phe
1               5                   10

<210> SEQ ID NO 69
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 69

Arg Pro Lys Pro Glu Glu Lys Arg Phe Leu
1               5                   10

<210> SEQ ID NO 70
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 70

Leu Leu Leu Ala Ser Ile Ala Ala Gly Leu
1               5                   10

<210> SEQ ID NO 71
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 71

Lys Cys Cys Lys Ile Arg Tyr Cys Asn Leu
1               5                   10

<210> SEQ ID NO 72
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 72

Phe Tyr Leu Lys Cys Cys Lys Ile Arg Tyr
1               5                   10

<210> SEQ ID NO 73
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 73

```
Gly Thr Met Ala Leu Leu Ala Leu Leu Leu
1               5                  10

<210> SEQ ID NO 74
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 74

Trp Ala Pro Leu Gly Thr Met Ala Leu Leu
1               5                  10

<210> SEQ ID NO 75
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 75

Gly Gly Leu Trp Leu Ala Ile Leu Leu Leu
1               5                  10

<210> SEQ ID NO 76
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 76

Met Gly Glu Ser Cys Gly Gly Leu Trp Leu
1               5                  10

<210> SEQ ID NO 77
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 77

Gly Ser Met Gly Glu Ser Cys Gly Gly Leu
1               5                  10

<210> SEQ ID NO 78
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 78

Gly Leu Trp Leu Ala Ile Leu Leu Leu Leu
1               5                  10

<210> SEQ ID NO 79
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 79

Pro Tyr Cys Val Ile Ala Ala Val Lys Ile
```

-continued

```
1               5                   10

<210> SEQ ID NO 80
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 80

Glu Tyr Ala Gly Ser Met Gly Glu Ser Cys
1               5                   10

<210> SEQ ID NO 81
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 81

Leu Leu Ala Leu Leu Leu Val Val Ala Leu
1               5                   10

<210> SEQ ID NO 82
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 82

Cys Gly Gly Leu Trp Leu Ala Ile Leu Leu
1               5                   10

<210> SEQ ID NO 83
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 83

Leu Gly Thr Met Ala Leu Leu Ala Leu Leu
1               5                   10

<210> SEQ ID NO 84
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 84

Leu Pro Arg Val Trp Thr Asp Ala Asn Leu
1               5                   10

<210> SEQ ID NO 85
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 85

Ser Cys Gly Gly Leu Trp Leu Ala Ile Leu
1               5                   10
```

<210> SEQ ID NO 86
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 86

Leu Ala Ser Ile Ala Ala Gly Leu Ser Leu
1               5                   10

<210> SEQ ID NO 87
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 87

Ser Tyr Glu Asn Asp Ile Ala Ser Met
1               5

<210> SEQ ID NO 88
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 88

Gly Phe Gln Leu Glu Asn Phe Thr Leu
1               5

<210> SEQ ID NO 89
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 89

Lys Thr Val Asn Glu Leu Gln Asn Leu
1               5

<210> SEQ ID NO 90
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 90

Lys Ile Pro Val Ser Gly Pro Phe Leu
1               5

<210> SEQ ID NO 91
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 91

Lys Pro Cys Asp Leu Pro Leu Arg Leu
1               5

```
<210> SEQ ID NO 92
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 92

Arg Phe Ala Gly Ala Ser Ile Lys Ile
1               5

<210> SEQ ID NO 93
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 93

Lys Gly Gly Lys Thr Val Asn Glu Leu
1               5

<210> SEQ ID NO 94
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 94

Lys Gln Lys Pro Cys Asp Leu Pro Leu
1               5

<210> SEQ ID NO 95
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 95

Ala Tyr Ile Pro Asp Glu Met Ala Ala
1               5

<210> SEQ ID NO 96
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 96

Leu Tyr Asn Pro Glu Arg Thr Ile Thr
1               5

<210> SEQ ID NO 97
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 97

Leu Tyr Ile Gly Asn Leu Ser Glu Asn
1               5
```

```
<210> SEQ ID NO 98
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 98

Lys Gln Gly Gln His Ile Lys Gln Leu
1               5

<210> SEQ ID NO 99
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 99

Lys Gln His Gln Gln Gln Lys Ala Leu
1               5

<210> SEQ ID NO 100
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 100

Ile Thr Ile Ser Pro Leu Gln Glu Leu
1               5

<210> SEQ ID NO 101
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 101

Ile Tyr Gly Lys Ile Lys Glu Glu Asn
1               5

<210> SEQ ID NO 102
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 102

Ala Ser Met Asn Leu Gln Ala His Leu
1               5

<210> SEQ ID NO 103
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 103

Gln Trp Glu Val Leu Asp Ser Leu Leu
1               5

<210> SEQ ID NO 104
```

```
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 104

Asp Cys Pro Asp Glu Ser Trp Ala Leu
1               5

<210> SEQ ID NO 105
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 105

Leu Gln Trp Glu Val Leu Asp Ser Leu
1               5

<210> SEQ ID NO 106
<211> LENGTH: 9
<212> TYPE: PRT
<213> ORGANISM: Artificial
<220> FEATURE:
<223> OTHER INFORMATION: An artificially synthesized peptide sequense.

<400> SEQUENCE: 106

Glu Ala Leu Ser Gly Lys Ile Glu Leu
1               5

<210> SEQ ID NO 107
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 107

Ile Tyr Gly Lys Ile Lys Glu Glu Asn Phe
1               5                   10

<210> SEQ ID NO 108
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 108

Lys Phe Thr Glu Glu Ile Pro Leu Lys Ile
1               5                   10

<210> SEQ ID NO 109
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 109

Arg Leu Ile Gly Lys Glu Gly Arg Asn Leu
1               5                   10

<210> SEQ ID NO 110
<211> LENGTH: 10
```

```
<212> TYPE: PRT
<213> ORGANISM: Artificial
<220> FEATURE:
<223> OTHER INFORMATION: An artificially synthesized peptide sequense.

<400> SEQUENCE: 110

Lys Ile Thr Ile Ser Pro Leu Gln Glu Leu
1               5                   10

<210> SEQ ID NO 111
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 111

Ser Tyr Glu Asn Asp Ile Ala Ser Met Asn
1               5                   10

<210> SEQ ID NO 112
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 112

Lys Pro Cys Asp Leu Pro Leu Arg Leu Leu
1               5                   10

<210> SEQ ID NO 113
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 113

Leu Tyr Asn Pro Glu Arg Thr Ile Thr Val
1               5                   10

<210> SEQ ID NO 114
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 114

Leu Tyr Ile Gly Asn Leu Ser Glu Asn Ala
1               5                   10

<210> SEQ ID NO 115
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 115

Val Ala Gln Arg Lys Ile Gln Glu Ile Leu
1               5                   10

<210> SEQ ID NO 116
<211> LENGTH: 10
<212> TYPE: PRT
```

-continued

```
<213> ORGANISM: Artificial
<220> FEATURE:
<223> OTHER INFORMATION: An artificially synthesized peptide sequense.

<400> SEQUENCE: 116

Leu Gln Ile Arg Asn Ile Pro Pro His Leu
1               5                   10

<210> SEQ ID NO 117
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 117

His Leu Gln Trp Glu Val Leu Asp Ser Leu
1               5                   10

<210> SEQ ID NO 118
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 118

Asn Leu Gln Ala His Leu Ile Pro Gly Leu
1               5                   10

<210> SEQ ID NO 119
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 119

Leu Ile Pro Gly Leu Asn Leu Asn Ala Leu
1               5                   10

<210> SEQ ID NO 120
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 120

Leu Gln Gln Pro Arg Gly Arg Arg Gly Leu
1               5                   10

<210> SEQ ID NO 121
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 121

Phe Thr Glu Glu Ile Pro Leu Lys Ile Leu
1               5                   10

<210> SEQ ID NO 122
<211> LENGTH: 10
<212> TYPE: PRT
<213> ORGANISM: Artificial
```

```
<220> FEATURE:
<223> OTHER INFORMATION: An artificially synthesized peptide sequense.

<400> SEQUENCE: 122

Glu Thr Val His Leu Phe Ile Pro Ala Leu
1               5                   10

<210> SEQ ID NO 123
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 123

Lys Leu Asn Gly Phe Gln Leu Glu Asn Phe
1               5                   10

<210> SEQ ID NO 124
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 124

Leu Ser Glu Asn Ala Ala Pro Ser Asp Leu
1               5                   10

<210> SEQ ID NO 125
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 125

Ile Pro Pro His Leu Gln Trp Glu Val Leu
1               5                   10

<210> SEQ ID NO 126
<211> LENGTH: 10
<212> TYPE: PRT
<213> ORGANISM: Artificial
<220> FEATURE:
<223> OTHER INFORMATION: An artificially synthesized peptide sequense.

<400> SEQUENCE: 126

Ser Ser Lys Asp Gln Ala Arg Gln Ala Leu
1               5                   10
```